United States Patent [19]
Elrod et al.

[11] Patent Number: 5,871,991
[45] Date of Patent: Feb. 16, 1999

[54] *ASPERGILLUS ORYZAE* 5-AMINOLEVULINIC ACID SYNTHASES AND NUCLEIC ACIDS ENCODING SAME

[75] Inventors: Susan L. Elrod; Joel R. Cherry, both of Davis, Calif.

[73] Assignee: Novo Nordisk BioTech, Inc., Davis, Calif.

[21] Appl. No.: 871,266

[22] Filed: Jun. 9, 1997

Related U.S. Application Data

[60] Provisional application No. 60/019,399, Jun. 10, 1996.
[51] Int. Cl.[6] .................................................. C12N 15/54
[52] U.S. Cl. ............................................... 435/193
[58] Field of Search .............................................. 435/193

[56] References Cited

U.S. PATENT DOCUMENTS 4,902,620   2/1990   Bard et al. .

FOREIGN PATENT DOCUMENTS 0 238 023   9/1987   European Pat. Off. .

OTHER PUBLICATIONS

Bradshaw et al., Current Genetics, vol. 23, pp. 501–507 (1993).
Urban–Grimal et al., Eur. J. Biochem, vol. 156, pp. 511–519 (1986).
XP 002045204, Asahi Chem Ind. Co. Ltd., Japanese Abstract of J 02167083 (Jun. 27, 1990).

*Primary Examiner*—Charles L. Patterson, Jr.
*Attorney, Agent, or Firm*—Steve T. Zelson; Elias J. Lambiris

[57] ABSTRACT

The present invention relates to *Aspergillus oryzae* 5-aminolevulinic acid synthases and isolated nucleic acid fragments comprising nucleic acid sequences encoding the 5-aminolevulinic acid synthases as well as nucleic acid constructs, vectors, and recombinant host cells comprising the nucleic acid sequences. The invention also relates to methods of producing the 5-aminolevulinic acid synthases.

8 Claims, 13 Drawing Sheets

```
ACCATTGACTCTCAAGCTATGGATCGTGCTCACCGTCTCGGCCAGACAAGACAGGTCACG 60
GTGTATCGCCTGATTACTCGCGGCACCATTGAGGAGCGTATTCGCAAGCGAGCTTTGCAG 120
AAGGAGGAAGTGCAGCGTGTCGTCATCTCAGGTGGCGCAGCTGGTGGGGTTGACTTCAAT 180
ACTCGCAACCGCGAGAGCCGAACCAAGGACATCGCCATGTGGCTGGCAGATGATGAACAG 240
GCGGAGCTTATTGAGCAAAAGGAGAAGGAAGCGCTGGACCGAGGCGAAGTGTTTGGCGCT 300
AGTAAAGGCGGGAAGAAGGCTGCTCAGAAGAGAAAGAGAGATATCACGCTGGATGATATG 360
TATCATGAAGGTATGTGAATCTGATCAAAGCTCTTCGTTCCGGGGAGGCTTCTGGAAATA 420
GTACTAACCGCGTCAATCTATAGGCGAAGGGAACTTTGACGATGCCAGTGCAAAGCCATC 480
AGGAGCGGCCACTCCTGTGTCGACTGCAGAGAATTTAGGCACCCCATCCTCCACGCCAGT 540
TCCTAAACGAGGACGTGGAAGGGGGACAGGAAAGGGCACGTCTAAAAGAGCCAAAACTAC 600
CAAGGAGAGATTACGTCTCATTGATGGCGACGGAGGCTTAGGGCCTAGTTGATTTAATCG 660
ATCTGTGCCTCAATAATGGACACGGCTGGTTATGGTCATGGCGTTCAGAGATTGCATTTC 720
TTTCCCACCCTTTATCTTTCTTTCTTTCCTCTTAAACCCCTCTTTTTTGTTTTTCTTTTT 780
ATCGGACTTTACTTGTGGGCAGCTTACGTTCTGCCTTGTATTAACAGCATATATTCCTGA 840
TTCCTGATGTACGAAGCGATTTAAGAGTCATTGAAGACGAAGGATGAAACCCGTGGTAAT 900
CAGCCGATAATGGCAAAGAGAAGGAGAAGAAAAAAATCAAGTGCGAGTTTTGAAATTGAT 960
GGCAAGATAGACATTGTATCCTGTACCTGTTCTTGGGCTGTGACGGGGGGGTGAAATTG 1020
ACGGTCATCACCCGGCTATTATTACTATTGTTGTACTGTACATCCGGATCCTGCTGGTCT 1080
GTATCTAGTTAGGGCAATATTCCCCGTCGCCAGGCCTCTTGGGTTATGAATGATTTCATA 1140
GGTGAAGTTTCGTATCCGTACGCACCGAGAGATTTCTTAGTATTACTTGTATTATGAAAA 1200
TGCACTTGCCGAGTTAAGTCCGCCGGCCAATCACGGCGGAGGATATGGTAAGCCGAAAAG 1260
TCTCGCCGAAGTCCCCGACTTACTCTTACTGGAAGTGGCTTAGTGCCCTCAGCGCCCCT 1320
CGCCCTCAGTCCATCAGCCAGATTGACTCTTATTTCTCTCTCCTCTTCGCCGCGGGTGAC 1380
ATATCCCTCTCCTTCTCCCTCTCCCTCTTGACAACATTTCATCTTCGCTTCCTTTTGTGA 1440
TATAGTCAGTTTCGCTATCCATTGAAGCATCACTCATGGAGTCTCTTCTCCAGCAGTCCC 1500
                                      M  E  S  L  L  Q  Q  S
GGGCGATGTGCCCGTTCCTTAAGCGCACATCTCCATCTTCTCTGCGTACGCTGGCAACCG 1560
 R  A  M  C  P  F  L  K  R  T  S  P  S  S  L  R  T  L  A  T
CGACTCGACCTAGCACTAGTTCCGGTGGAGGCACTATGTCTAATCTCCAGGTCATTGCCC 1620
 A  T  R  P  S  T  S  S  G  G  G  T  M  S  N  L  Q  V  I  A
GTCGCTGCCCTGTCATGAGCAAGGCTCTGGCCGTGCAGAGCGCTCGCATGGCCGGTACCA 1680
 R  R  C  P  V  M  S  K  A  L  A  V  Q  S  A  R  M  A  G  T
AAAGATTCACCTCATGTGCTGCCGGCATCACCGGTCTCGGCAACAAGCATTGCCGTGCTC 1740
 K  R  F  T  S  C  A  A  G  I  T  G  L  G  N  K  H  C  R  A
CTACTGGGAAGAGAACCCTGCACTCCACCTCCGGTAACGGCGCCAATGTGAGCGCAGAGA 1800
 P  T  G  K  R  T  L  H  S  T  S  G  N  G  A  N  V  S  A  E
TCTACAAGAACACCCAGCGAGATCCCGCCGGTTTCTCGAAGATCAAGACCCCTGCCAATG 1860
 I  Y  K  N  T  Q  R  D  P  A  G  F  S  K  I  K  T  P  A  N
CTACCGCCGCTGCCGCTACGTCTGGCCCTCGTCCAGAGGCTCCCGTGGCGAAGCCTTTCA 1920
 A  T  A  A  A  A  T  S  G  P  R  P  E  A  P  V  A  K  P  F
ACTACAATTCTTTCTACAACACCGAATTGGAAAAGAAACACAAGGACAAGTCGTATCGCT 1980
 N  Y  N  S  F  Y  N  T  E  L  E  K  K  H  K  D  K  S  Y  R
ATTTCAACAACATCAATCGTCTCGCTCAGGAGTTTCCCCGGGCTCACACCACATCTGCCG 2040
 Y  F  N  N  I  N  R  L  A  Q  E  F  P  R  A  H  T  T  S  A
AGGAACGTGTGACGGTCTGGTGCTCGAACGATTATCTCGGCATGGGCCGCAACCCCGAGG 2100
 E  E  R  V  T  V  W  C  S  N  D  Y  L  G  M  G  R  N  P  E
TTCTGGCCACCATGCATAAGACATTGGACACCTACGGAGCCGGTGCGGGAGGTACTCGCA 2160
 V  L  A  T  M  H  K  T  L  D  T  Y  G  A  G  A  G  G  T  R
ACATTTCAGGTCACAATCAACATGCCGTGAGCCTGGAGAACACCCTGGCCAAATTGCACG 2220
 N  I  S  G  H  N  Q  H  A  V  S  L  E  N  T  L  A  K  L  H
GCAAGGAGGCGGCATTAGTCTTCAGCTCATGCTTCGTGGCTAACGATGCCACCCTCGCAA 2280
 G  K  E  A  A  L  V  F  S  S  C  F  V  A  N  D  A  T  L  A
CCCTGGGTAGCAAGTTGCCCGACTGTGTTATTCTGTCCGATAGCCTGAATCATGCATCGA 2340
 T  L  G  S  K  L  P  D  C  V  I  L  S  D  S  L  N  H  A  S
TGATTCAGGGTATTCGCCATTCAGGCGCCAAGAAAATGGTTTTCAAGCATAATGATCTGG 2400
 M  I  Q  G  I  R  H  S  G  A  K  K  M  V  F  K  H  N  D  L
```

FIG. 3A

```
TCGACCTTGAGGCCAAGTTGGCAGCTCTACCTCTTCATGTCCCCAAGATTATTGCATTCG 2460
 V  D  L  E  A  K  L  A  A  L  P  L  H  V  P  K  I  I  A  F
AATCAGTTTATAGCATGTGCGGATCTATTGCCCCAATTGAGAAGATCTGTGATCTTGCAG 2520
 E  S  V  Y  S  M  C  G  S  I  A  P  I  E  K  I  C  D  L  A
ACAAGTACGGTGCCATTACTTTCCTGGATGAAGTCCACGCTGTGGGAATGTACGGACCTC 2580
 D  K  Y  G  A  I  T  F  L  D  E  V  H  A  V  G  M  Y  G  P
ACGGAGCAGGTGTGGCAGAGCACCTTGACTATGACATCTATGCTTCCCAAGATACGGTCA 2640
 H  G  A  G  V  A  E  H  L  D  Y  D  I  Y  A  S  Q  D  T  V
ACCCGCGCAGTACTAAGGGAACCGTGATGGACCGAATCGATATTATCACCGGTACTCTGG 2700
 N  P  R  S  T  K  G  T  V  M  D  R  I  D  I  I  T  G  T  L
GCAAGGCCTACGGATGTGTCGGGGGCTACATTGCTGGATCCGCTGCGATGGTTGACACCA 2760
 G  K* A  Y  G  C  V  G  G  Y  I  A  G  S  A  A  M  V  D  T
TCCGCTCCCTCGCCCCTGGCTTCATCTTCACCACGTCCTTGCCGCCCGCCACCATGGCTG 2820
 I  R  S  L  A  P  G  F  I  F  T  T  S  L  P  P  A  T  M  A
GTGCAGACACTGCTATCCAGTACCAGGCTCGTCACCAGGGCGACCGCGTCCTGCAGCAGT 2880
 G  A  D  T  A  I  Q  Y  Q  A  R  H  Q  G  D  R  V  L  Q  Q
TGCACACCCGCGCGGTCAAAGCAGCTTTCAAGGAGTTGGATATTCCTGTAATTCCCAACC 2940
 L  H  T  R  A  V  K  A  A  F  K  E  L  D  I  P  V  I  P  N
CCTCCCATATCATTCCGCTCCTGGTTGGGGATGCCGAGGTTGCTAAGAAGGCCTCGGACA 3000
 P  S  H  I  I  P  L  L  V  G  D  A  E  V  A  K  K  A  S  D
AGCTTCTGGAGGAGCATGGAATTTATGTACAAGCCATCAACTACCCAACCGTGCCTCGGG 3060
 K  L  L  E  E  H  G  I  Y  V  Q  A  I  N  Y  P  T  V  P  R
GTGAAGAGCGGCTTCGTATCACGCCCACCCCGGGACATATCAAGGAGCACCGCGACCACC 3120
 G  E  E  R  L  R  I  T  P  T  P  G  H  I  K  E  H  R  D  H
TGGTGCAAGCCGTCCAAACAGTCTGGAACGAACTGGGCATCAAACGCACCAGCGATTGGG 3180
 L  V  Q  A  V  Q  T  V  W  N  E  L  G  I  K  R  T  S  D  W
AAGCGCAAGGCGGCTTCGTCGGCGTGGGTGTCGATGGCGCCGAGGCTGAGAACCAGCCGA 3240
 E  A  Q  G  G  F  V  G  V  G  V  D  G  A  E  A  E  N  Q  P
TTTGGAATGATGTGCAGCTGGGGCTGAAGGAAAACGAAGCCATTGAGGCTGCTGTGGAAC 3300
 I  W  N  D  V  Q  L  G  L  K  E  N  E  A  I  E  A  A  V  E
GCGAGTTTGCCGAGGCCCCCATGCGGACCGCCACCCGTCCTGCCGCGGCTGCTGCTTCGT 3360
 R  E  F  A  E  A  P  M  R  T  A  T  R  P  A  A  A  A  S
CAATCCCGGTGGGTGTGGCTGCCTGAAGTGGCTGCCCGCATGTGAGCTGAAATCGACGTG 3420
 S  I  P  V  G  V  A  A  .
GAATTCTATACACACACACACACACACACACACACACACACACACACACACACACACACA 3480
CACACACACACACACACACTAACACACACTATGTTATAAATTCCACATCCACTCCTTTGT 3540
CCCTTGTTGGACGTAATTGGTATTTGGACTATTAGTTAGAACCAGTCAGTCGTTACCATG 3600
TGTTTCGGTTCGACTCGAAATCTGACATGTTGTCTGCCCCATGCCACTTCATCTCCTCC 3660
GTAACCGCAGGGCTTCAAATACACTGCCCAGTAATTGTAGTCAATATAGCAGTTAACTAA 3720
CCTTCACCAATTTCCTAATAACAATAGAAGGGGCCATACACGCAGTACCAAAGATCACCT 3780
ACCTCCGATCAATATCCGAACCTCAGGCTACATACATCAAGTCGCATTAATCGATTCCGA 3840
CCTCTGTTTATCCCTGAAAATAACTAAGATCATGATCTACGTTTGGTAAGTGGGACACCT 3900
ACCTACACTGGGAGGTATTGAATAAAGGCATCATTCATATAGTCACAAGATGCCAGGGCC 3960
AATTCATGATATGGATAGCTACTTCCAAACATAATTCAGAGGTATCATTCTGCTCTTCAG 4020
ACAGTTCTTCTCGAAGATCAGTAGGAGCCAGTTTTGACCATTAACTTGTAATGTAATTGC 4080
GATTGTAGTAGATCCGAGATCCATTCACTTTCTAAGGGTTAATTGATTCATTTTACTGAT 4140
ACCTCACCCACCATATT                                          4157
```

FIG. 3B

```
A. oryzae          M E S - - - - L L Q Q S R A M C P F L K R T S P S S L R T L   26
A. nidulans        M E A - - - - L L Q Q S R A M C P F L K R S S P N T L R S L   26
chicken erythroid  M A A - - - - F L - - - - - R C P L L A R H P P L A - R A F   20
human erythroid    M V T A A M L L Q - - - - - C C P V L A R G P T S L L G K V   25
mouse erythroid    M V A A A M L L W - - - - - S C P V L S Q G P T G L L G K V   25
chicken hepatic    M E A - - - V V R - - - - - R C P F L A R V S Q A F L Q K V   22
human hepatic      M E S - - - V V R - - - - - R C P F L S R V P Q A F L Q K A   22
rat hepatic        M E T - - - V V R - - - - - R C P F L S R V P Q A F L Q K A   22

A. oryzae          A - - - - - - - T - - - - - A T R P S T S S G G G T M S N L   44
A. nidulans        A - - - - - - - T - - - - - A T R P S T S P G G G T M T N L   44
chicken erythroid  A - - - - - - - T - - - - - G A - - - - - - - - - - - - - -   24
human erythroid    V K T H Q F L F G - - - - - I G - - - - - - - - - - - - - -   36
mouse erythroid    A K T Y Q F L F S - - - - - I G - - - - - - - - - - - - - -   36
chicken hepatic    G - - - - - - - P S L L F Y A Q - - - - - - - - - - - - - -   31
human hepatic      G - - - - - - - K S L L F Y A Q - - - - - - - - - - - - - -   31
rat hepatic        G - - - - - - - K S L L F Y A Q - - - - - - - - - - - - - -   31

A. oryzae          Q V I A R R C P V M S - - - - - - - - - - K A L A V Q S A     63
A. nidulans        Q R I A R R C P V M S - - - - - - - - - - K A L A V Q S A     63
chicken erythroid  - - - - - R C P F M G - - - - - - - - - - F A - H R A A P     37
human erythroid    - - - - - R C P I L A T Q G P N C S Q I H L K A - T K A G G   60
mouse erythroid    - - - - - R C P I L A T Q G P T C S Q I H L K A - T K A G G   60
chicken hepatic    - - - - - H C P K M - - - - - - - - - - - E A - A P P A A     44
human hepatic      - - - - - N C P K M - - - - - - - - - - - E V - G A K P A     44
rat hepatic        - - - - - N C P K M - - - - - - - - - - - E V - G A K P A     44

A. oryzae          - - - - - - - - - - - - - - - R - - M                         65
A. nidulans        - - - - - - - - - - - - - - - R - - M                         65
chicken erythroid  - - - - - - - - - - - - - - - E - - L                         39
human erythroid    D S P S W A K G H C P F M L S E - - L Q D G K S K I V Q - K   87
mouse erythroid    - - - - - - - - - - - - - - E - - L Q D R K S K I V Q - R     72
chicken hepatic    - - - - - - - - - - - - - - - A R G L A T S A S R G Q Q V E   59
human hepatic      - - - - - - - - - - - - - - - P R A L S T A A V H Y Q Q I K   59
rat hepatic        - - - - - - - - - - - - - - - P R T V S T S A A Q C Q Q V K   59

A. oryzae                                                                        65
A. nidulans                                                                      65
chicken erythroid                                                                39
human erythroid    A A P E V Q E D V K A F K T D L P S S L V S V S - - L R - -  113
mouse erythroid    A A P E V Q E D V K T F K T D L L S T M D S T T - - R S - -   98
chicken hepatic    E T P A A Q P E A K K A K E V A Q Q N T D G S Q - - P P - -   85
human hepatic      E T P P A S E K D K T A K A K V Q Q T P D G S Q - - Q S P D   87
rat hepatic        E T P P A N E K E K T A K A A V Q Q A P D E S Q M A Q T P D   89

A. oryzae                                                                        65
A. nidulans                                                                      65
chicken erythroid                                                                39
human erythroid    - - - - - K P F S G P Q E Q E Q I S G K V T H L I Q N - N M  137
mouse erythroid    - - - - - H S F P S F Q E P E Q T E G A V P H L I Q N - N M  122
chicken hepatic    - - - - - A G H P P A A A V Q S S A T K C P F L A A Q M N H  110
human hepatic      G T Q L P S G H P L P A T S Q G T A S K C P F L A A Q M N Q  117
rat hepatic        G T Q L P P G H P S P S T S Q S S G S K C P F L A A Q L A R  119

A. oryzae                                                                        65
A. nidulans                                                                      65
chicken erythroid                                                                39
human erythroid    P G N Y V F S Y D - - Q F F R                                150
mouse erythroid    T G S Q A F G Y D - - Q F F R                                135
chicken hepatic    K S S N V F C K A - - S L E L                                123
human hepatic      R G S S V F C K A - - S L E L                                130
rat hepatic        R A A A S S A R P V W S F R R                                134
```

FIG. 4

```
A. oryzae     M - - E S L L Q Q S R A M C P F L K R T S P S S L R T L A T  28
A. nidulans   M - - E A L L Q Q S R A M C P F L K R S S P N T L R S L A T  28
human         M V T A A M L L Q - - - C C P V L A R G P T S L L G K V V K  27
S. cerevisae  M - - Q - - - - - - - - - - - - - - - - - - - R S I F A      7

A. oryzae     A T R P S T S S G G G T M S N L Q V I A R R C P V M S - K A  57
A. nidulans   A T R P S T S P G G G T M T N L Q R I A R R C P V M S - K A  57
human         T H Q F L F G I G - - - - - - - - - - - - R C P I L A T Q G  45
S. cerevisae  - - - - - - - - - - - - - - - - - - - - - - - - - - - -      7

A. oryzae     L A V Q S A R M A G T K R F T S C A A G I T G L G N - - - K  84
A. nidulans   L A V Q S A R M T G T K R F T S S A A G V P G A G A G T P K  87
human         P N C S Q I H L K A T K A G G D S P S W A K G H C P F M L S  75
S. cerevisae  - - - - - - - - - - - R F G N S S A A V S T L N R L S T T    25

A. oryzae     H C R A P T G K R T L H S T S G N G A N V S A E I Y K N T Q  114
A. nidulans   P T R G S P G K R A L H S T G G N G A N M S T E F H K G A Q  117
human         E L Q D G K S K - I V Q K A A P E V Q E D V K A F K T D L P  104
S. cerevisae  A - - A P H A K N G Y A T A T G A G A A A A T A - - - - -    47

A. oryzae     R D P A G F S K I K T P A N A T A A A A T S G P R P E - - -  141
A. nidulans   Q I H P G L S N A - T R S H V G A S A T V S G P T P R - - -  143
human         S S L V S V S L R K P F S G P Q E Q E Q I S G K V T H L I Q  134
S. cerevisae  - - - - - - - - - - T A S S T H A A A A A A A A A N H - - -  64

A. oryzae     - - A P V A K P F N Y N S F Y N T E L E K K H K D K S Y R Y  169
A. nidulans   - - A P V A A P F D Y D A F Y N A E L Q K K H Q D K S Y R Y  171
human         N N M P G N Y V F S Y D Q F F R D K I M E K K Q D H T Y R V  164
S. cerevisae  - - S T Q E S G F D Y E G L I D S E L Q K K R L D K S Y R Y  92

A. oryzae     F N N I N R L A Q E F P R A H T - - - - T S A E R V T V W    195
A. nidulans   F N N I N R L A Q E F P R A H T - - - - A S K D E K V T V W  197
human         F K T V N R W A D A Y P F A Q H F F E A S V A S K D V S V W  194
S. cerevisae  F N N I N R L A K E F P L A H R - - - - Q R E A D K V T V W  118

A. oryzae     C S N D Y L G M G R N P E V L A T M H K T L D T Y G A G A G  225
A. nidulans   C S N D Y L G M G R N P E V L A T M H K T L D T Y G A G A G  227
human         C S N D Y L G M S R H P Q V L Q A T Q E T L Q R H G A G A G  224
S. cerevisae  C S N D Y L A L S K H P E V L D A M H K T I D K Y G C G A G  148

A. oryzae     G T R N I S G H N Q H A V S L E N T L A K L H G K E A A L V  255
A. nidulans   G T R N I S G H N Q H A V S L E N T L A K L H G K E A A L V  257
human         G T R N I S G T S K F H V E L E Q E L A E L H Q K D S A L L  254
S. cerevisae  G T R N I A G H N I P T L N L E A E L A T L H K K E G A L V  178
```

FIG. 5A

```
A. oryzae      FSSCFVANDATLATLGSKLPDCVILSDSLN  285
A. nidulans    FSSCFVANDATLATLGSKMPDCVILSDSLN  287
human          FSSCFVANDSTLFTLAKILPGCEIYSDAGN  284
S. cerevisae   FSSCYVANDAVLSLLGQKMKDLVIFSDELN  208

A. oryzae      HASMIQGIRHSGAKKMVFKHNDLVDLEAKL  315
A. nidulans    HASMIQGIRHSGRKKMVFKHNDLVDLETKL  317
human          HASMIQGIRNSGAAKFVFRHNDPDHLKKLL  314
S. cerevisae   HASMIVGIKHANVKKHIFKHNDLNELEQLL  238

A. oryzae      AALPLHVPKIIAFESVYSMCGSIAPIEKIC  345
A. nidulans    ASLPLHVPKIIAFESVYSMCGSIAPIEAIC  347
human          EKSNPKIPKIVAFETVHSMDGAICPLEELC  344
S. cerevisae   QSYPKSVPKLIAFESVYSMAGSVADIEKIC  268

A. oryzae      DLADKYGAITFLDEVHAVGMYGPHGAGVAE  375
A. nidulans    DLADKYGAITFLDEVHAVGMYGPHGAGVAE  377
human          DVSHQYGALTFVDEVHAVGLYGSRGAGIGE  374
S. cerevisae   DLADKYGALTFLDEVHAVGLYGPHGAGVAE  298

A. oryzae      HLDYDIYASQDTVNPRST-KG---TVMDRI  401
A. nidulans    HLDYEIYASQDTANPLST-KG---TVMDRI  403
human          R-----------------------DGIMHKI  382
S. cerevisae   HCDFESHRASGIATPKTNDKGAKTVMDRV  328

A. oryzae      DIITGTLGKAYGCVGGYIAGSAAMVDTIRS  431
A. nidulans    NIITGTLGKAYGCVGGYIAGSAALVDTIRS  433
human          DIISGTLGKAFGCVGGYIASTRDLVDMVRS  412
S. cerevisae   DMITGTLGKSFGSVGGYVAASRKLIDWFRS  358

A. oryzae      LAPGFIFTTSLPPATMAGADTAIQYQARHQ  461
A. nidulans    LAPGFIFTTSLPPATMAGADTAIRYQARHQ  463
human          YAAGFIFTTSLPPMVLSGALESVRLLKGEE  442
S. cerevisae   FAPGFIFTTTLPPSVMAGATAAIRYQRCHI  388
```

FIG. 5B

```
A. oryzae    G D - - R V L Q Q L H T R A V K A A F K E L D I P V I P N P  489
A. nidulans  Q D - - R I L Q Q L H T R A V K Q S F K D L D I P V I P N P  491
human        G Q A L R R A H Q R N V K H M R Q L L M D R G L P V I P C P  472
S. cerevisae D L - - R T S Q Q K H T M Y V K K A F H E L G I P V I P N P  416

A. oryzae    S H I I P L L V G D A E V A K K A S D K L L E E H G I Y V Q  519
A. nidulans  S H I V P L L V G D A E L A K Q A S D K L L E E H G I Y V Q  521
human        S H I I P I R V G N A A L N S K L C D L L L S K H G I Y V Q  502
S. cerevisae S H I V P V L I G N A D L A K Q A S D I L I N K H Q I Y V Q  446

A. oryzae    A I N Y P T V P R G E E R L R I T P T P G H I K E H R D H L  549
A. nidulans  A I N Y P T V P R G E E R L R I T P T P G H T Q E L R D H L  551
human        A I N Y P T V P R G E E L L R L A P S P H H S P Q M M E D F  532
S. cerevisae A I N F P T V A R G T E R L R I T P T P G H T N D L S D I L  476

A. oryzae    V Q A V Q T V W N E L G I K R T S D W E A Q G G F V G V G V  579
A. nidulans  V E A V N T V W N D L G I K R A S D W K A M G G F V G V G V  581
human        V E K L L L A W T A V G L P - - - - - - - - - - L Q D V S V  552
S. cerevisae I N A V D D V F N E L Q L P R V R D W E S Q G G L L G V G -  505

A. oryzae    D G A E A E N Q P I W N D V Q L G L K E N E A I E A A V E R  609
A. nidulans  E A A E L E N Q P I W T D A Q L N M R P D E T L E A A V E R  611
human        A A C N F C R R P V - - - - - H F E L M S E - - - - - - W E R  572
S. cerevisae E S G F V E E S N L W T S S Q L S L T N D D L N - - - - - - -  529

A. oryzae    E F A E A - - - - - - - - - - - - P M R T A T R P A A A A A S S  629
A. nidulans  E F Q A A V P G M K A G G A K A K P V G S I A A N P I G A S  641
human        S Y F G N M - - - - - - - - - - - - - - - - - - - - - - - G  579
S. cerevisae - - - - - - - P N V R D P I V K Q L E V S S - - - - - - - - -  544

A. oryzae    I P V G V A - A                                              636
A. nidulans  I P V A A A A Z                                              649
human        P Q Y V T T Y A                                              587
S. cerevisae - - - - G I K Q                                              548
```

FIG. 5C

ASPERGILLUS ORYZAE 5-AMINOLEVULINIC ACID SYNTHASES AND NUCLEIC ACIDS ENCODING SAME

CROSS-REFERENCE TO RELATED APPLICATIONS

This application is a continuation-in-part of application Ser. No. 60/019,399 filed Jun. 10, 1996, the contents of which are fully incorporated herein by reference.

BACKGROUND OF THE INVENTION

1. Field of the Invention

The present invention relates to *Aspergillus oryzae* 5-aminolevulinic acid synthases and isolated nucleic acid fragments comprising nucleic acid sequences encoding the 5-aminolevulinic acid synthases. The invention also relates to nucleic acid constructs, vectors, and host cells comprising the nucleic acid sequences as well as methods for producing the 5-aminolevulinic acid synthases.

2. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps. The first enzyme in the biosynthetic pathway is 5-aminolevulinic acid synthase which catalyzes the condensation of glycine and succinyl-CoA to form 5-aminolevulinic acid. In the biosynthesis of heme in liver cells and differentiating erythrocytes, 5-aminolevulinic acid synthase is a key regulatory enzyme.

The conversion of an apoprotein into a hemoprotein depends on the availability of heme provided by the heme biosynthetic pathway. The apoprotein form of the hemoprotein combines with heme to produce the active hemoprotein. The active hemoprotein acquires a conformation which makes the hemoprotein more stable than the apoprotein to proteolytic attack. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by *Aspergillus oryzae* (WO 93/19195). While heme supplementation of a fermentation medium results in a significant improvement in the yield of a hemoprotein, it is non-kosher, costly, and difficult to implement on a large scale.

The cloning and sequencing of a 5-aminolevulinic acid synthase gene from *Aspergillus nidulans* (Bradshaw et al., 1993, *Current Genetics* 2233:501–507) have been disclosed.

It is an object of the present invention to provide new 5-aminolevulinic acid synthases and genes encoding same.

SUMMARY OF THE INVENTION

The present invention relates to substantially pure 5-aminolevulinic acid synthases obtained from *Aspergillus oryzae* and to isolated nucleic acid fragments comprising a nucleic acid sequence which encodes an *Aspergillus oryzae* 5-aminolevulinic acid synthase. The present invention further provides nucleic acid constructs, vectors, and recombinant host cells comprising a nucleic acid fragment of the present invention as well as methods for producing the 5-aminolevulinic acid synthases.

BRIEF DESCRIPTION OF THE FIGURES

FIGS. 3A–3B shows the nucleotide and deduced amino acid sequences of an *Aspergillus oryzae* 5-aminolevulinic acid synthase gene (SEQ ID NOS: 1 and 2, respectively). Potentially important transcriptional sites, CCAAT box and TATA box are underlined. The two conserved putative HRM motifs are boxed; the glycine loop involved in pyridoxal phosphate co-factor binding is circled and the important lysine is indicated with an asterisk.

FIG. 4 shows the conserved heme regulatory motifs in various 5-aminolevulinic acid synthase genes. The pentapeptide motifs are boxed.

FIGS. 5A–5C shows the alignment of the deduced amino acid sequences for 5-aminolevulinic acid synthases from *Aspergillus oryzae, Aspergillus nidulans, Saccharomyces cerevisiae* and human erythroid (SEQ ID NOS: 2, 16, 17 and 18, respectively). Conserved amino acids are boxed.

DETAILED DESCRIPTION OF THE INVENTION

Figure 1:
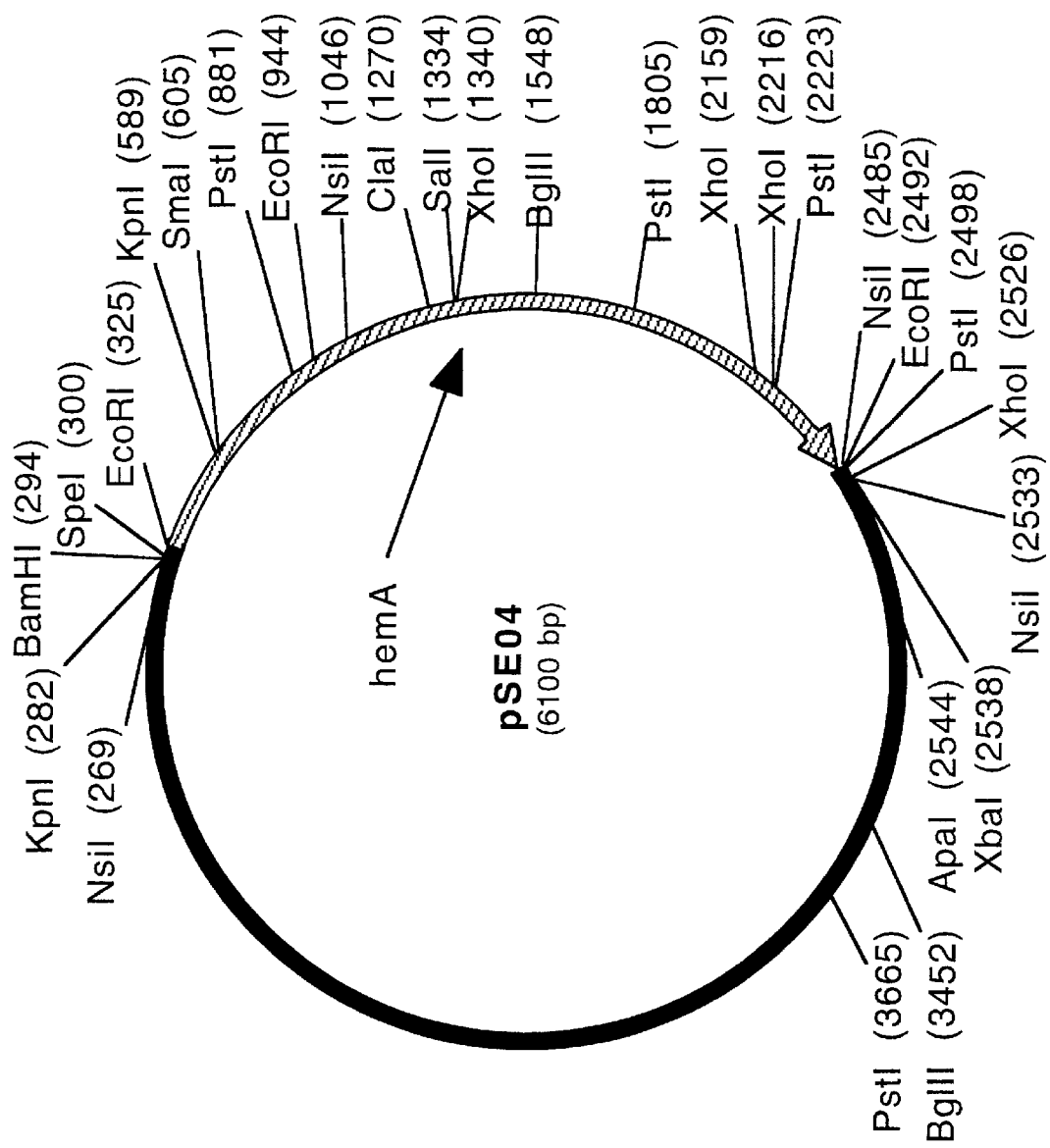
FIG. 1 shows a restriction map of plasmid pSE04.

The present invention, as mentioned above, relates to 5-aminolevulinic acid synthases obtained from an *Aspergillus oryzae* strain. Strains of this species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), International Mycological Institute (IMI), Agricultural Research Service Patent Culture Collection, Northern Regional Research Center (NRRL), and Institute for Fermentation in Osaka, Japan (IFO).

In a preferred embodiment, the present invention relates to 5-aminolevulinic acid synthases obtained from Aspergillus oryzae or a mutant strain thereof. In a more preferred embodiment, the present invention relates to 5-aminolevulinic acid synthases obtained from Aspergillus oryzae IFO 4177 or a mutant strain thereof, e.g., the 5-aminolevulinic acid synthase having the amino acid sequence set forth in SEQ ID NO:2.

The present invention also relates to 5-aminolevulinic acid synthases which are encoded by nucleic acid sequences which are capable of hybridizing under high stringency conditions (i.e., prehybridization and hybridization at 45° C. in 5 X SSPE, 0.3% SDS, 200 μg/ml sheared and denatured salmon sperm DNA, and 50% formamide) with a probe which hybridizes with the nucleic acid sequence set forth in SEQ ID NO:1 under the same conditions. The gene, or an oligonucleotide based thereon, can be used as a probe in Southern hybridization to isolate homologous genes of any Aspergillus species. In particular, such probes can be used for hybridization with the genomic or cDNA of the species of interest, following standard Southern blotting procedures, in order to identify and isolate the corresponding 5-aminolevulinic acid synthase gene therein. Degenerate PCR primers (oligonucleotides) can be used with genomic DNA or cDNA segments to amplify 5-aminolevulinic acid synthase-specific gene segments.

Identification and isolation of 5-aminolevulinic acid synthase genes from a source other than those specifically exemplified herein can be achieved by utilization of the methodology described in the present examples, with publicly available Aspergillus strains.

For purposes of the present invention, the term "obtained from" means that the 5-aminolevulinic acid synthase is produced by a specific source, e.g., an Aspergillus strain, or by a cell in which a gene from the source encoding the 5-aminolevulinic acid synthase has been inserted.

The invention also encompasses 5-aminolevulinic acid synthase variants which have at least about 80%, preferably about 85%, more preferably about 90%, and most preferably about 95% homology with the amino acid sequence set forth in SEQ ID NO:2, and which qualitatively retains the activity of the 5-aminolevulinic acid synthases described herein. The present invention is also directed to 5-aminolevulinic acid synthase variants which have an amino acid sequence which differs by three amino acids, preferably by two amino acids, and more preferably by one amino acid from the amino acid sequence set forth in SEQ ID NO:2. Each difference may be an insertion or deletion of an amino acid or the substitution of an amino acid residue by a different amino acid. Useful variants within the categories defined above include, for example, ones in which conservative amino acid substitutions have been made, which substitutions do not significantly affect the activity of the protein. By conservative substitution is meant that amino acids of the same class may be substituted by any other amino acid of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

The physical-chemical properties of the 5-aminolevulinic acid synthases of the present invention may be determined using various techniques well known in the art including, but not limited to, SDS-PAGE, isoelectric focusing, and cross-reaction immunoidentity tests. The 5-aminolevulinic acid synthases of the present invention may be assayed using methods known in the art.

The 5-aminolevulinic acid synthases of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, for example, *Protein Purification*, eds. J.-C. Janson and Lars Ryden, VCH Publishers, New York, 1989). As defined herein, a "substantially pure" 5-aminolevulinic acid synthase is a 5-aminolevulinic acid synthase which is essentially free of other non-5-aminolevulinic acid synthase proteins, for example, at least about 20% pure, preferably about 40% pure, more preferably about 60% pure, even more preferably about 80% pure, most preferably about 90% pure, and even most preferably at least about 95% pure, as determined by SDS-PAGE.

The present invention also relates to nucleic acid fragments comprising a nucleic acid sequence which encodes a 5-aminolevulinic acid synthase of the present invention and to nucleic acid constructs comprising a nucleic acid fragment of the present invention.

In a preferred embodiment, the nucleic acid sequence encodes a 5-aminolevulinic acid synthase obtained from *Aspergillus oryzae*. In a more preferred embodiment, the nucleic acid sequence encodes a 5-aminolevulinic acid synthase obtained from *Aspergillus oryzae* IFO 4177, e.g., the nucleic acid sequence set forth in SEQ ID NO:1. The present invention also encompasses nucleic acid sequences which encode a 5-aminolevulinic acid synthase having the amino acid sequence set forth in SEQ ID NO:2, which differ from SEQ ID NO:1 by virtue of the degeneracy of the genetic code. The nucleic acid sequences of the present invention encompass both the genomic sequence depicted therein as well as the corresponding cDNA and RNA sequences, and the phrase "nucleic acid sequence" as used herein will be understood to encompass all such variations including synthetic DNA.

The present invention also relates to nucleic acid constructs comprising a nucleic acid fragment of the invention. "Nucleic acid construct" shall generally be understood to mean a nucleic acid molecule, either single- or double-stranded, which is isolated from a naturally occurring gene or which has been modified to contain segments of nucleic acid which are combined and juxtaposed in a manner which would not otherwise exist in nature. In a preferred embodiment, the nucleic acid constructs are operably linked to regulatory regions capable of directing the expression of the 5-aminolevulinic acid synthase in a suitable expression host.

The present invention also provides recombinant vectors comprising a nucleic acid construct of the present invention. In a preferred embodiment, the nucleic acid sequence is operably linked to a promoter sequence. In another preferred embodiment, the vectors of the present invention further comprise a transcription termination signal and/or a selectable marker.

The recombinant vectors of the invention are useful for the expression of an *Aspergillus oryzae* 5-aminolevulinic acid synthase gene in active form. A useful vector contains an element that permits stable integration of the vector into the host cell genome or autonomous replication of the vector in a host cell independent of the genome of the host cell, and preferably one or more phenotypic markers which permit easy selection of transformed host cells. The vector may also include control sequences such as a promoter, ribosome binding site, translation initiation signal, and, optionally, a selectable marker or various activator or repressor sequences. To permit the secretion of the expressed protein, nucleic acids encoding a signal sequence may be inserted prior to the coding sequence of the gene. For expression under the direction of control sequences, a 5-aminolevulinic acid synthase gene to be used according to the present invention is operably linked to the control sequences in such a way that expression of the coding sequence is achieved under conditions compatible with the control sequences.

The vectors carrying a nucleic acid construct of the present invention may be any vector which can conveniently be subjected to recombinant DNA procedures. The choice of a vector will typically depend on the host cell into which the vector is to be introduced. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. Alternatively, the vector may be one which, when introduced into a host cell, is integrated into the host cell genome and replicated together with the chromosome(s) into which it has been integrated. The vector system may be a single vector or plasmid or two or more vectors or plasmids which together contain the total DNA to be integrated into the genome.

In the vectors, the DNA sequence should be operably linked to a suitable promoter sequence. The promoter may be any DNA sequence which shows transcriptional activity in the host cell of choice and may be obtained from genes encoding proteins either homologous or heterologous to the host cell. Examples of suitable promoters for directing the transcription of the nucleic acid construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes, the prokaryotic β-lactamase promoter (Villa-Kamaroff et al., 1978, *Proceedings of the National Academy of Sciences U.S.A.* 75:3727–373 1) or the tac promoter (DeBoer et al., 1983, *Proceedings of the National Academy of Sciences U.S.A.* 80:21–25). Further promoters are described in "Useful proteins from recombinant bacteria" in *Scientific American*, 1980, 242:74–94; and in Sambrook et al., *Molecular Cloning, A Laboratory Manual*, 2d ed., Cold Spring Harbor, N.Y., 1989. In a yeast host, a useful promoter is the eno-1 promoter. For transcription in a fungal host, examples of useful promoters are those obtained from the genes encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Particularly preferred promoters are the TAKA amylase, NA2-tpi (a hybrid of the promoters from the genes encoding *Aspergillus niger* neutral α-amylase and *Aspergillus oryzae* triose phosphate isomerase), and glaA promoters.

The vectors of the invention may also comprise a suitable transcription terminator and, in eukaryotes, polyadenylation sequences operably connected to the DNA sequence encoding a 5-aminolevulinic acid synthase of the present invention. Termination and polyadenylation sequences may be obtained from the same sources as the promoter. The vectors may further comprise a DNA sequence enabling the vectors to replicate in the host cell in question. Examples of such sequences are the origins of replication of plasmids pUC19, pACYC177, pUB110, pE194, pAMB1, and pIJ702.

The vectors of the present invention preferably contain one or more selectable markers which permit easy selection of transformed cells. A selectable marker is a gene the product of which provides for biocide or viral resistance, resistance to heavy metals, prototrophy to auxotrophs and the like. The selectable marker may be selected from the group consisting of, but not limited to, amdS, pyrG, argB, niaD, sC, trpC, bar, and hygB. Preferred for use in an Aspergillus cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243 where the selectable marker is contained in a separate vector.

The vectors of the invention preferably also contain a signal peptide coding region, which codes for an amino acid sequence linked to the amino terminus of the heme biosynthetic enzyme, permitting the localization of the 5-aminolevulinic acid synthase to a particular cellular compartment. The signal peptide coding region may be native to the first nucleic acid sequence encoding the 5-aminolevulinic acid synthase or may be obtained from foreign sources. The 5' end of the coding sequence of the first nucleic acid sequence may inherently contain a signal peptide coding region naturally linked in translation reading frame with the segment of the coding region which encodes the localized 5-aminolevulinic acid synthase. Alternatively, the 5' end of the coding sequence may contain nucleic acids encoding a signal peptide coding region which is foreign to that portion of the coding sequence which encodes the localized heme biosynthetic enzyme. The signal peptide coding region may be obtained from a *Neurospora crassa* ATPase gene (Viebrock et al., 1982, *EMBO Journal* 1:565–571) or from a *Saccharomyces cerevisiae* cytochrome c peroxidase gene (Kaput et al., 1982, *Journal of Biological Chemistry* 257:15054–15058). However, any signal peptide coding region capable of permitting localization of the 5-aminolevulinic acid synthase in a filamentous fungal host of choice may be used in the present invention.

To avoid the necessity of disrupting the cell to obtain the expressed 5-aminolevulinic acid synthase, and to minimize the amount of possible degradation of the expressed 5-aminolevulinic acid synthase within the cell, it is preferred that expression of the 5-aminolevulinic acid synthase gene gives rise to a product secreted outside the cell. To this end, the 5-aminolevulinic acid synthases of the present invention may thus comprise a preregion permitting secretion of the expressed protein into the culture medium. If desirable, this preregion may be native to the 5-aminolevulinic acid synthase of the invention or substituted with a different preregion or signal sequence, conveniently accomplished by substitution of the DNA sequences encoding the respective preregions. For example, the preregion may be obtained from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf prepro-chymosin gene. Particularly preferred is the preregion for *Aspergillus oryzae* TAKA amylase, *Aspergillus niger* neutral amylase, the maltogenic amylase from Bacillus NCIB 11837, *Bacillus stearothermophilus* α-amylase, or *Bacillus licheniformis* subtilisin. An effective signal sequence for fungal hosts is the *Aspergillus oryzae* TAKA amylase signal, the *Rhizomucor miehei* aspartic proteinase signal, or the *Rhizomucor miehei* lipase signal.

The procedures used to ligate the nucleic acid construct of the invention, the promoter, terminator and other elements, and to insert them into suitable vectors containing the information necessary for replication, are well known to persons of ordinary skill in the art (cf., for instance, Sambrook et al., supra).

The present invention also relates to host cells comprising a nucleic acid construct or an expression vector of the invention which are advantageously used in the recombinant production of the 5-aminolevulinic acid synthases of the invention. The cell may be transformed with the nucleic acid construct of the invention, conveniently by integrating the construct into the host chromosome. This integration is generally considered to be an advantage as the sequence is more likely to be stably maintained in the cell. Integration of the construct into the host chromosome may be performed according to conventional methods, e.g., by homologous or non-homologous recombination. Alternatively, the cell may be transformed with an expression vector as described below in connection with the different types of host cells.

The choice of host cells and vectors will to a large extent depend upon the 5-aminolevulinic acid synthase and its source. The host cell may be selected from prokaryotic cells, such as bacterial cells. Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram-negative bacteria such as *E. coli.* The transformation of the bacteria may, for instance, be effected by protoplast transformation or by using competent cells in a manner known per se.

The host cell is preferably a eukaryote, such as a mammalian cell, an insect cell, a plant cell or preferably a fungal cell, including yeast and filamentous fungi. For example, useful mammalian cells include CHO or COS cells. A yeast host cell may be selected from a species of Saccharomyces or Schizosaccharomyces, e.g., *Saccharomyces cerevisiae.* Useful filamentous fungi may be selected from a species of Aspergillus, e.g., *Aspergillus oryzae* or *Aspergillus niger.* Alternatively, a strain of a Fusarium species, e.g., *Fusarium oxysporum* or *Fusarium graminearum,* can be used as a host cell. Fungal cells may be transformed by a process involving protoplast formation, transformation of the protoplasts, and regeneration of the cell wall in a manner known per se. A suitable procedure for transformation of Aspergillus host cells is described in EP 238 023. A suitable method of transforming Fusarium species is described by Malardier et al., 1989, Gene 78:147–156 or in copending U.S. Ser. No. 08/269,449.

In a particularly preferred embodiment, the expression of the 5-aminolevulinic acid synthase gene is achieved in a fungal host cell, such as Aspergillus. The 5-aminolevulinic acid synthase gene is ligated into a plasmid preferably containing the *Aspergillus oryzae* TAKA amylase promoter or the *Aspergillus niger* neutral amylase NA2 promoter and amdS or pyrG as the selectable marker. Alternatively, the selectable marker may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, *Proceedings of the National Academy of Sciences U.S.A.* 81:1470–1474.

The present invention also relates to methods for producing a 5-aminolevulinic acid synthase of the present invention comprising (a) cultivating an *Aspergillus oryzae* strain in a nutrient medium to produce the 5-aminolevulinic acid synthase, and (b) recovering the 5-aminolevulinic acid synthase.

The present invention also relates to methods for recombinantly producing a 5-aminolevulinic acid synthase of the present invention comprising (a) fermenting a host cell comprising a nucleic acid construct comprising a nucleic acid sequence encoding the 5-aminolevulinic acid synthase under conditions conducive to the production of the enzyme, and (b) recovering the 5-aminolevulinic acid synthase. If the expression system secretes the 5-aminolevulinic acid synthase into the fermentation medium, the enzyme can be recovered directly from the medium. If the recombinant 5-aminolevulinic acid synthase is not secreted, it is recovered from cell lysates.

Any method of cultivation of a cell known in the art may be used which results in the expression or isolation of a 5-aminolevulinic acid synthetase of the present invention. For example, cultivation may be understood as comprising shake flask cultivation, small- or large-scale fermentation (including continuous, batch, fed-batch, or solid state fermentations) in laboratory or industrial fermentors performed in a suitable medium and under conditions allowing the 5-aminolevulinic acid synthase to be expressed or isolated. The cultivation takes place in a suitable nutrient medium comprising carbon and nitrogen sources and inorganic salts using procedures known in the art (see, e.g., Bennett, J. W. and LaSure, L. (eds.), *More Gene Manipulations in Fungi,* Academic Press, California, 1991). Suitable media are available from commercial suppliers or may be prepared according to published compositions (e.g., in catalogues of the American Type Culture Collection).

The 5-aminolevulinic acid synthases produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

The present invention is also directed to methods of using the 5-aminolevulinic acid synthases.

The 5-aminolevulinic acid synthases of the present invention may be used to convert glycine and succinyl-CoA to 5-aminolevulinic acid which is useful as a herbicide.

The 5-aminolevulinic acid synthases of the present invention may be also used to increase the yield of a hemoprotein produced by a host cell, where 5-aminolevulinic acid synthase is a rate-limiting step in the production of heme in the host cell, by overexpressing the nucleic acid sequence encoding the 5-aminolevulinic acid synthase in the host cell. The method comprises:

(a) introducing into the host cell, which is capable of producing the hemoprotein, one or more copies of the nucleic acid sequence encoding the 5-aminolevulinic acid synthase, wherein the nucleic acid sequence is operably linked to regulatory regions capable of directing the expression of the 5-aminolevulinic acid synthase;

(b) cultivating the cell in a nutrient medium suitable for production of the hemoprotein and the 5-aminolevulinic acid synthase; and (c) recovering the hemoprotein from the nutrient medium of the cell.

The present invention is further described by the following examples which should not be construed as limiting the scope of the invention.

EXAMPLES

Example 1

*Aspergillus oryzae* strain A1560 genomic DNA extraction

*Aspergillus oryzae* strain A1560 (IFO 4177) was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3M solution) was added to a final concentration of 0.3M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 µg/ml and the mixture was incubated at 37û° C. for 30 minutes. Proteinase K was then added at a concentration of 200 µg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 2

Construction of plasmid pSE04

Genomic DNA was obtained from *Aspergillus nidulans* strain A26 (Fungal Genetics Stock Center, Kansas City, Kans.) using the same procedure described in Example 1. Plasmid pSE04 was constructed by ligation of PCR fragments from an amplification reaction containing *Aspergillus nidulans* A26 genomic DNA. The amplification reaction contained the following components: 50 ng of *Aspergillus nidulans* A26 genomic DNA, 100 µM each of dATP, dCTP, dGTP, and dTTP (Boehringer Mannheim, Indianapolis, Ind.), 50 pmoles of primers ALAS3d 5'-TTTATGATGGAGGCCCTTCTCCAGCAGTCTC-3' (SEQ ID NO:3) and ALAS4e 5'-CTATGCATTTAAGCAGCAGCCGCGACTGG-3' (SEQ ID NO:4), 2 units of Taq DNA polymerase (Perkin-Elmer Corp., Branchburg, N.J.), and 1X Taq DNA polymerase buffer (Perkin-Elmer Corp., Branchburg, N.J.). The reaction was incubated in a Perkin-Elmer Thermal Cycler (Perkin-Elmer Corp., Branchburg, N.J.) programmed for 30 cycles each at 95° C. for 1 minute, 55° C. for 1 minute, and 72° C. for 90 seconds. The 2 kb PCR product was isolated by excision after electrophoresis using a 1.1% low melting temperature agarose gel (FMC, Rockland, Me.) with 40 mM Tris-acetate-1 mM disodium EDTA (TAE) buffer, and subcloned into the pCRII vector (Invitrogen, San Diego, Calif.) according to the manufacturer's instructions to produce pSE04 (FIG. 1).

Example 3

*Aspergillus oryzae* strain A1560 DNA libraries and identification of ALA synthase (hemA) clones

*Aspergillus oryzae* strain A1560 genomic DNA libraries were constructed using the bacteriophage cloning vector λZipLox (Life Technologies, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged using commercial packaging extracts (Stratagene, La Jolla, Calif.). The packaged DNA libraries were plated and amplified in *E. coli* Y1090ZL cells. The unamplified genomic library contained $1 \times 10^6$ pfu/ml.

Figure 2:
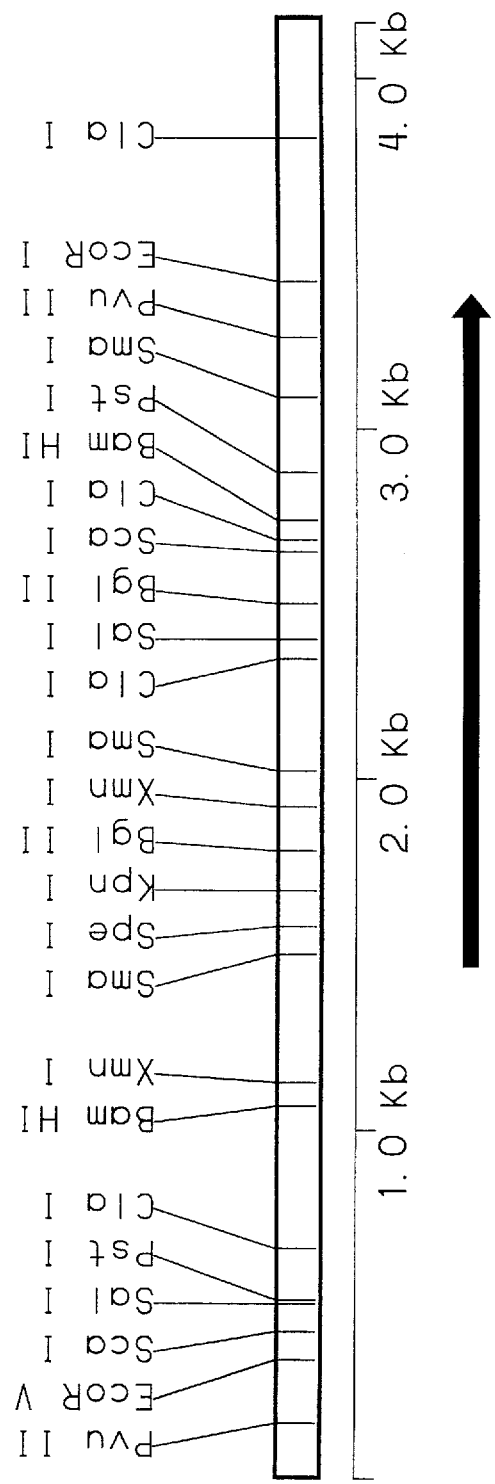
FIG. 2 shows a restriction map of a 4.2 kb genomic fragment containing an *Aspergillus oryzae* 5-aminolevulinic acid synthase gene. Scale in kilobases (kb) is shown under the map. The arrow represents the location of the open reading frame of the gene.

Bacteriophage DNA from $7 \times 10^4$ plaques was transferred to duplicate circular Nytran Plus membranes (Schleicher & Schuell, Keene, N.H.) and probed with a digoxigenin (DIG)-labeled probe which was prepared by PCR amplification of *Aspergillus nidulans* hemA genomic DNA from plasmid pSE04 described in Example 2. The amplification reaction contained the following components: 1X DIG probe synthesis mix (Boehringer Mannheim, Indianapolis, Ind.), 100 µM each of DATP, dCTP, dGTP, and dTTP, 50 pmoles of primer ALAS3d and primer ALAS4e described in Example 2, 2 units of Taq DNA polymerase, and 1X Taq DNA polymerase buffer. The reaction was incubated in a Perkin-Elmer Thermal Cycler programmed for 30 cycles each at 95° C. for 1 minute, 55° C. for 1 minute, and 72° C. for 2 minutes. Denatured probe was added to the hybridization buffer at a concentration of 2 ng/ml and incubated overnight with prehybridized membranes. Prehybridization and hybridization was conducted at 42° C. in 5 X SSC, 0.1% sarkosyl, 0.02% SDS, 1% Genius blocking agent (Boehringer Mannheim, Indianapolis, Ind.), and 30% formamide. Membranes were washed twice in 5 X SSC-0.1% SDS followed by two washes in 2 X SSC-0.1% SDS. Each wash was performed for 15 minutes at room temperature. The washed membrane was exposed to Kodak X-OMAT AR film for approximately 2 hours at room temperature followed by development using a Konica QX-70 automatic film processor according to the manufacturer's instructions. Primary plaques were purified and screened a second time. Five clones were identified and excised into pZL derivatives according to the manufacturer's instructions (Bethesda Research Laboratories, Inc., Gaithersburg, Md.). The pZL derivatives were designated *E. coli* DH5α pSE11, pSE13, pSE15, pSE17, and pSE20. These clones were found to overlap and span a 4.2 kb region for which the restriction map is shown in FIG. 2.

Example 4

Southern hybridization of *Aspergillus oryzae* strain A1560 genomic DNA with a 5-aminolevulinic acid synthase (hema) probe

*Aspergillus oryzae* strain A1560 genomic DNA (10 µg) prepared as described in Example 1 was restriction digested with either BamHI or EcoRI. The fragments were separated by electrophoresis on a 1% agarose-TBE gel. DNA was transferred to a Nytran Plus membrane in 0.4N NaOH using a TurboBlot apparatus (Schleicher & Schuell, Keene, N.H.) according to the manufacturer's instructions. The membrane was prehybridized for 2 hours at 42° C. in 5 X SSC, 0.1% sarkosyl, 0.02% SDS, 1% Genius blocking agent (Boehringer Mannheim, Indianapolis, Ind.), and 50% formamide in a Hybaid oven (Labnet, Woodbridge, N.J.). Hybridization was accomplished with a DIG-labeled hemA probe generated by PCR amplification as described in Example 3, except the hemA clone pSE17 was used as a template with primer hemA5' 5'-TCATTTAAATGATGGAGTCTCTTCTCC-3' (SEQ ID NO:5) and primer hemA3' 5'-TCTTAATTAATCAGCTCACATGCGGG-3' (SEQ ID NO:6). DIG-labeled hemA probe (1 ng probe/ml of solution) was added to fresh hybridization buffer and incubated with the membrane overnight at 42° C. Subsequently, the membrane was washed twice for 15 minutes each at room temperature in 5 X SSC-0.1% SDS followed by two washes under the same conditions in 2 X SSC-0.1% SDS. The washed membrane was exposed to Kodak X-OMAT AR film for approximately 2 hours at room temperature followed by development using a Konica QX-70 automatic film processor according to the manufacturer's instructions.

Southern blot hybridization of *Aspergillus oryzae* genomic DNA with the *Aspergillus oryzae* hemA probe showed the presence of hybridization signals consistent with a single gene copy number. A 1.7 kb band observed in the BamHI lane was predicted from the restriction map (FIG. 2).

Example 5

Characterization of *Aspergillus oryzae* A1560 5-aminolevulinic acid synthase (hemA) gene

*E. coli* DH5α pSE17 described in Example 3 was subjected to DNA sequencing according to the following procedure. DNA sequencing was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38:47–60) using the M13 reverse (–48) and M13 forward (–20) primers (New England Biolabs, Beverly, Mass.) and primers unique to the DNA being sequenced.

The nucleotide sequence of the cloned gene revealed an open reading frame of 1911 nucleotides as shown in FIG. 3 (SEQ ID NO:1). The coding sequence does not contain any introns which was confirmed by cDNA cloning and sequence analysis which is in contrast to the *Aspergillus nidulans* hemA gene which contains one intron at its 5' end (Bradshaw et al., 1993, *Current Genetics* 23:501–507). The 5' untranslated sequence contains several pyrimidine-rich and AT-rich regions as in other fungal genes (Gurr et al., 1987, In Kinghorn, J. R. (ed.), *Gene Structure in Eukaryotic Microbes,* pp. 93–139, IRL Press, Oxford), a CCAAT sequence at position –249, and a putative TATA box located at position –35. The CCAAT sequence is a consensus binding site for transcriptional regulators which modulate transcription in response to oxygen, such as the Hap2/3/4 transcriptional regulatory complex in yeast and humans (Olesen and Guarente, 1990, *Molecular and Cellular Biology* 12:2302–2314). This regulatory complex is also conserved in mammals, and a CCAAT-binding activity has been identified in *Aspergillus nidulans* (Davis et al., 1993, *Genetica* 90:133–145). The importance of this sequence in the *Aspergillus oryzae* hemA gene is not known and, due to limited sequence information, has not been confirmed in the *Aspergillus nidulans* hemA 5' region (Bradshaw et al., 1993, supra). Transcriptional regulation of the *Aspergillus oryzae* hemA gene in response to oxygen is not currently known, but the *Aspergillus nidulans* hemA gene does not appear to be transcriptionally regulated even under conditions of oxygen limitation (Bradshaw et al., 1993, supra). Interestingly, the yeast HEM1 gene is also constitutively expressed, but its expression is controlled by a balance between positive and negative regulatory sites (Keng and Guarente, 1987, *Proceedings of the National Academy of Sciences U.S.A.* 84:9113–9117). An $(AC)_{35}$ repeat motif occurs in the 3' untranslated region. Similar repeats have also been observed in subtelomeric, intron, and promoter regions of mammalian and yeast genes and have no known function, although they have been implicated in gene amplification events (Passananti et al., 1987, *EMBO Journal* 6:1697–1703).

The deduced amino acid sequence of the *Aspergillus oryzae* strain A1560 gene product is shown in FIG. 3 (SEQ ID NO:2). The nucleotide sequence encodes a predicted protein of 636 amino acids with a molecular weight of 68 kDa. Since this enzyme is located in the mitochondria, the N-terminus is predicted to contain a mitochondrial leader sequence. In fact, the first 35 amino acids are rich in serine, threonine, lysine, and arginine residues consistent with a function as a mitochondrial leader. A potential heme regulatory motif (HRM) occurs in the presumed mitochondrial leader sequences of both the *Aspergillus nidulans* and *Aspergillus oryzae* hemA sequences (FIG. 4). HRMs localized to leader sequences are believed to prevent import of 5-aminolevulinic acid synthase proteins into the mitochondria in mouse via direct interactions with heme (Lathrop and Timko, 1993, *Science* 259:522–525; Zhang and Guarente, 1995, *EMBO Journal* 14:313–320). A second potential HRM also occurs in the beginning of the putative mature protein sequence. It is probable that the HRMs play a role in the regulation of 5-aminolevulinic acid synthase activity. Interestingly, the *Saccharomyces cerevisiae* 5-aminolevulinic acid synthase protein sequence does not contain any putative HRMs and does not appear to be a key regulatory step in yeast heme biosynthesis (Labbe-Bois and Labbe, In Daley, Harry A., ed., *Biosynthesis of Heme and Chlorophylls,* 1990, McGraw Hill Publishers, New York, pp 235–285).

Overall, the deduced amino acid sequence as shown in FIG. 5 shares 81% identity with the *Aspergillus nidulans* hemA gene (SEQ ID NO:16), 57% identity with the *Saccharomyces cerevisiae* HEM1 gene (SEQ ID NO:17; Urban-Grimal, 1986, *European Journal of Biochemistry* 156:511–519), and 51% identity with the human erythroid hem1 (ALAS2) gene (SEQ ID NO: 18; Bishop, 1990, *Nucleic Acids Research* 18:7187–7188) which were determined using the Applied Biosystems GeneAssist program (blosum62.mat matrix). However, the highest degree of conservation occurs in the C-terminal two-thirds of the protein which contains the catalytic domain. Furthermore, the lysine and glycine-loop, important for catalytic activity and pyridoxal phosphate co-factor binding in other 5-aminolevulinic acid synthase enzymes (Ferreira et al., 1995, *Journal of Bioenergetics and Biomembranes* 27:151–159; Ferreira, 1995, *Protein Science* 4:1001–1006) are also highly conserved.

Example 6

Construction of plasmid pSE31

Figure 6:
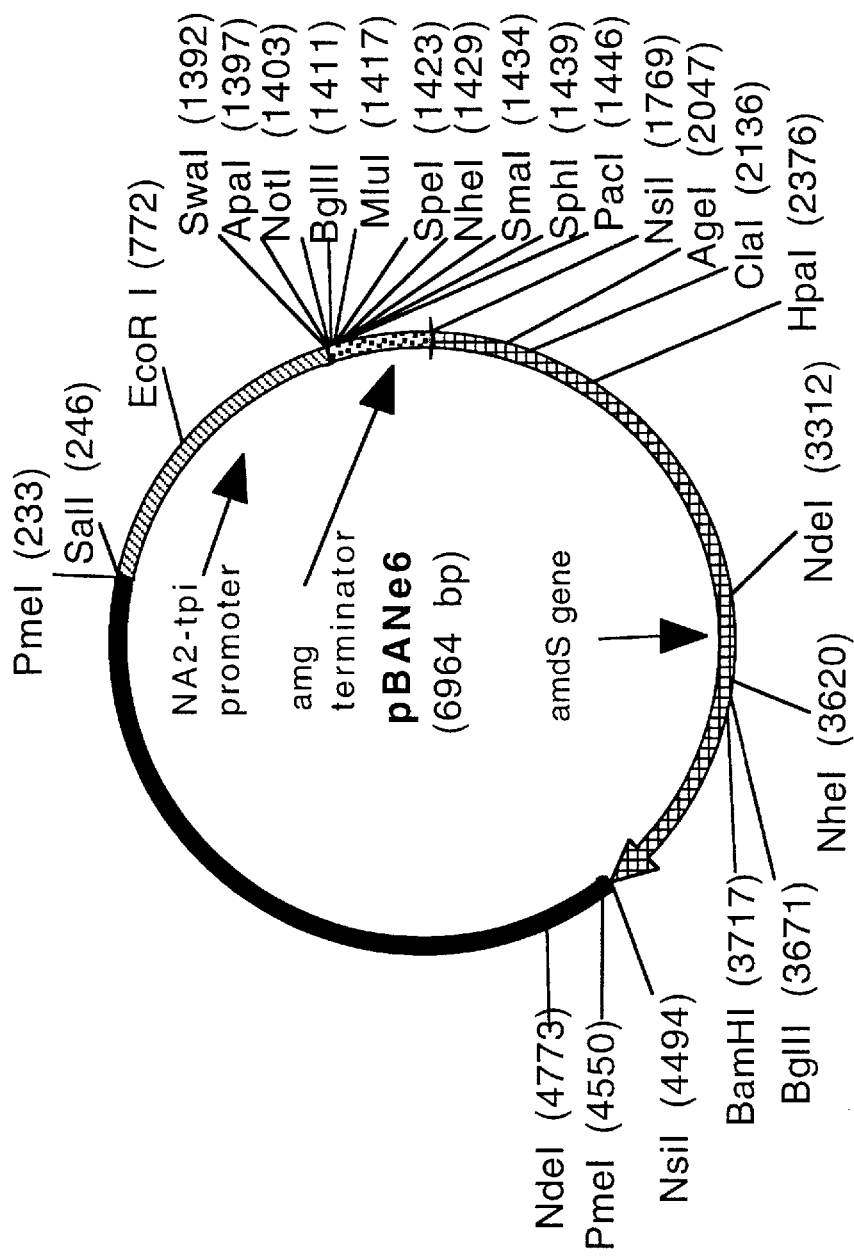
FIG. 6 shows a restriction map of plasmid pBANe6.
Figure 7:
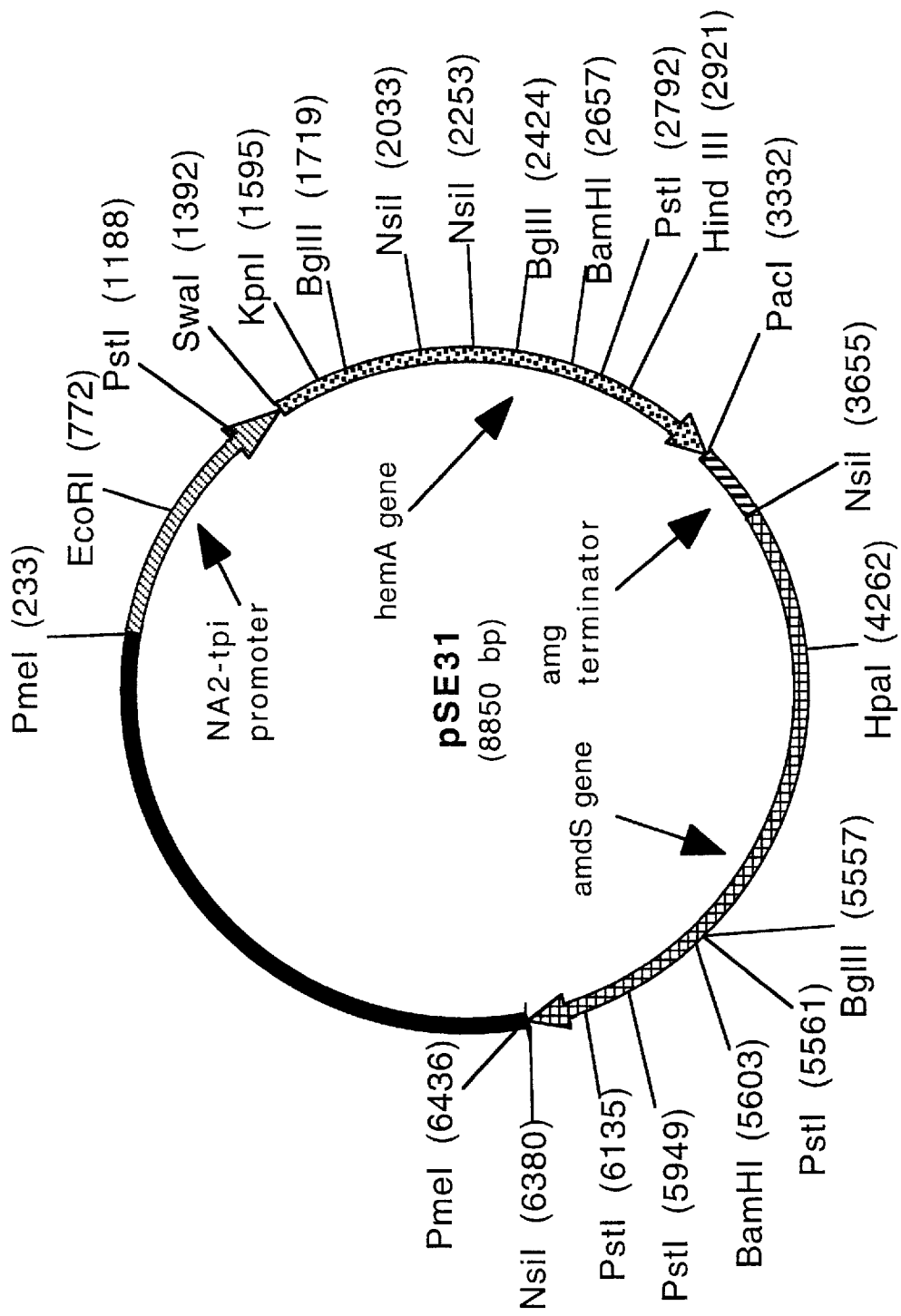
FIG. 7 shows a restriction map of plasmid pSE31.

Plasmid pSE31 was constructed by directional cloning of PCR-amplified *Aspergillus oryzae* hemA DNA into pBANe6 (FIG. 6). The PCR amplification reaction was performed using DNA from hemA clone *E. coli* DH5α pSE17 described in Example 3 where the reaction contained the following components: 50 ng of pSE17, 2 units of Vent DNA polymerase (New England Biolabs, Beverly, Mass.), 1 X Vent DNA polymerase buffer (New England Biolabs, Beverly, Mass.), 400 μM each of dATP, dCTP, dGTP, and dTTP (Boehringer Mannheim, Indianapolis, Ind.), and 50 pmoles of primer hemA5' 5'-TCATTTAAATGATGGAGTCTCTTCTCC-3' (SEQ ID NO:5) and primer hemA3' 5'-TCTTAATTAATCAGCTCACATGCGGG-3' (SEQ ID NO:6). The reaction was incubated in a Perkin-Elmer Thermal Cycler programmed for 30 cycles each at 95° C. for 1 minute, 55° C. for 1 minute, and 72° C. for 90 seconds. Primer hemA5' contains a SwaI site (underlined) and primer hemA3' contains a PacI site (underlined) which were used for cloning into pBANe6 digested with SwaI and PacI to produce pSE31 (FIG. 7).

Example 7

Construction of Aspergillus oryzae strain JRoC50.3.18A

Aspergillus oryzae strain JRoC50.3.18A containing plasmid pJROC50 was constructed as follows. Coprinus cinereus IFO 8371 peroxidase cDNA fragments were prepared by PCR using specific oligonucleotide primers shown below (Saiki et al., 1988, Science 239:487–491) constructed on the basis of the amino acid sequence of the Coprinus macrorhizus peroxidase (Baunsgaard et al., 1993, European Journal of Biochemistry 213:605–611):

1. 5'-GCGCGAATTCGTNGGNATNGGNATNAA(CT)CA(CT)GG-3' (SEQ ID NO:7)

2. 3'-TACAGNTT(GA)AC(GA)GGNGGCCTAGGCG-5' (SEQ ID NO:8)

3. 5'-GCGAATTCACNCCNCA(GA)GTNTT(CT)GA(CT)AC-3' (SEQ ID NO:9)

4. 3'-GGNAA(GA)GGNCCNCT(CT)AA(GA)CCTAGGCG-5' (SEQ ID NO: 10)

5. 5'-GCGCGAATTCTGGCA(GA)TCNAC-3' (SEQ ID NO:11)

6. 5'-GCGCGAATTCTGGCA(GA)AGNATG-3' (SEQ ID NO:12)

7. 3'-CGNTACCGNTT(CT)TACAGCCTAGG-5' (SEQ ID NO:13)

PCR was performed using the Gene Amp Kit and apparatus (Perkin Elmer Cetus, Norwalk, Conn.) in accordance with the manufacturer's instructions with the exception that the reaction was conducted at 28° C. for the first 3 cycles in order to obtain better hybridization to the first strand cDNA (prepared from mRNA obtained from Coprinus cinereus strain IFO 8371) and subsequently at 65° C. for 30 cycles of PCR.

The primers were combined as follows: 1 with 2; 3 with 4; 5 with 7; 6 with 7; 1 with 4; and 3 with 7. The PCR fragments were extended with an EcoRI site at the 5'-end and a BamHI site at the 3'-end. The reactions were analyzed on a 1% agarose-TBE gel where bands of the expected size were found in all the reactions. To verify that the bands corresponded to peroxidase-specific sequences, the gel was subjected to Southern blotting and hybridized to an oligonucleotide probe with the following sequence which is positioned between primers 3 and 4:

5'-GT(CT)TC(GA)AT(GA)TAGAA(CT)TG-3' (SEQ ID NO:14)

The probe was found to hybridize to bands of approximately 130 bp, 420 bp, 540 bp, and 240 bp, thus confirming that the DNA bands observed corresponded to peroxidase sequences.

DNA from the various PCR reactions was digested with EcoRI and BamHI and cloned into the plasmid pUC19 (New England BioLabs, Beverly, Mass.). Colonies containing the correct PCR fragments were identified by hybridization using the oligonucleotide probe (SEQ ID NO: 14) described above. DNA from positive colonies was analyzed by restriction mapping and partial DNA sequence analysis as described by Sanger et al. (1977, Proceedings of the National Academy of Sciences U.S.A. 74:5463–5467). A 430 bp fragment from one of the clones, obtained by using primers 1 and 4, was used to screen a Coprinus cinereus cDNA library as described below.

Figure 8:
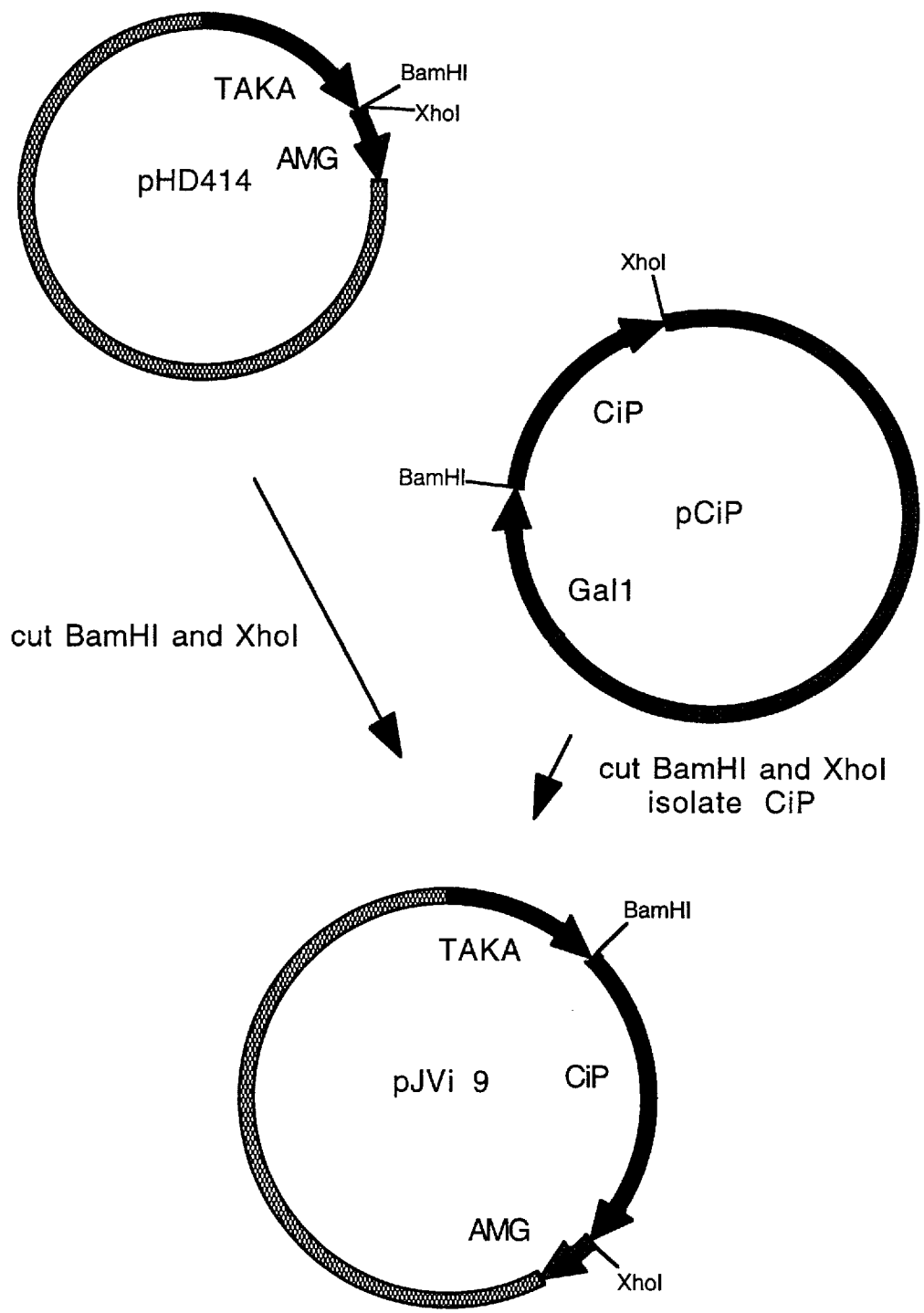
FIG. 8 shows the construction of plasmid pJVi9.

Total RNA was extracted from homogenized Coprinus cinereus strain IFO 8371 mycelia, collected at the time of maximum peroxidase activity according to the methods described by Boel et al. (1984, EMBO Journal 3:1097–1102) and Chirgwin et al. (1979, Biochemistry 18:5294–5299). Poly(A)-containing RNA was obtained by two cycles of affinity chromatography on oligo(dT)-cellulose as described by Aviv and Leder (1972, Proceedings of the National Academy of Sciences U.S.A. 69:1408–1412). cDNA was synthesized by means of a cDNA Synthesis Kit (Invitrogen, San Diego, Calif.) according to the manufacturer's instructions. Approximately 50,000 E. coli recombinants from the Coprinus cinereus cDNA library were transferred to Whatman 540 paper filters. The colonies were lysed and immobilized as described by Gerger et al. (1979, Nucleic Acids Research 7:2115–2135). The filters were hybridized with the $^{32}$P-labelled 430 bp peroxidase-specific probe in 0.2 X SSC-0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Bimboim and Doly, 1979, Nucleic Acids Research 7:1513–1523), and the DNA sequences of the cDNA inserts were determined by the Sanger dideoxy procedure (Sanger et al., 1977, Proceedings of the National Academy of Sciences U.S.A. 74:5463–5467). One of the colonies was selected and the vector was designated pCiP. The peroxidase cDNA fragment was excised from the vector by cleavage with BamHI/XhoI and was purified by agarose gel electrophoresis, electroeluted and made ready for ligation reactions. The cDNA fragment was ligated to BamHI/XhoI digested pHD414 to generate pJVi9 wherein the cDNA was under transcriptional control of the TAKA promoter from Aspergillus oryzae and the AMG™ (Novo Nordisk A/S, Bagsværd, Denmark) terminator from Aspergillus niger as shown in FIG. 8.

Figure 9:
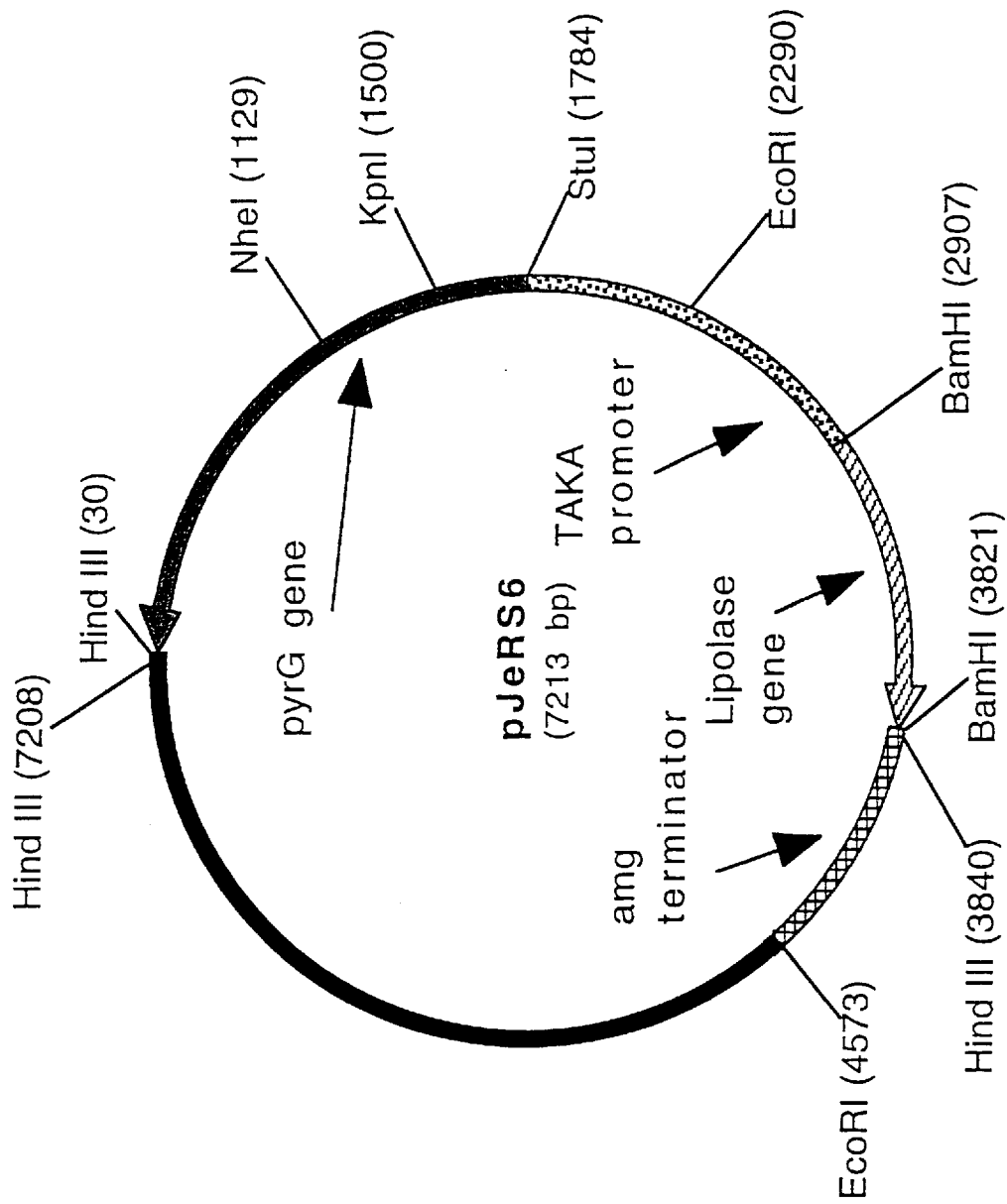
FIG. 9 shows a restriction map of plasmid pJeRS6.
Figure 10:
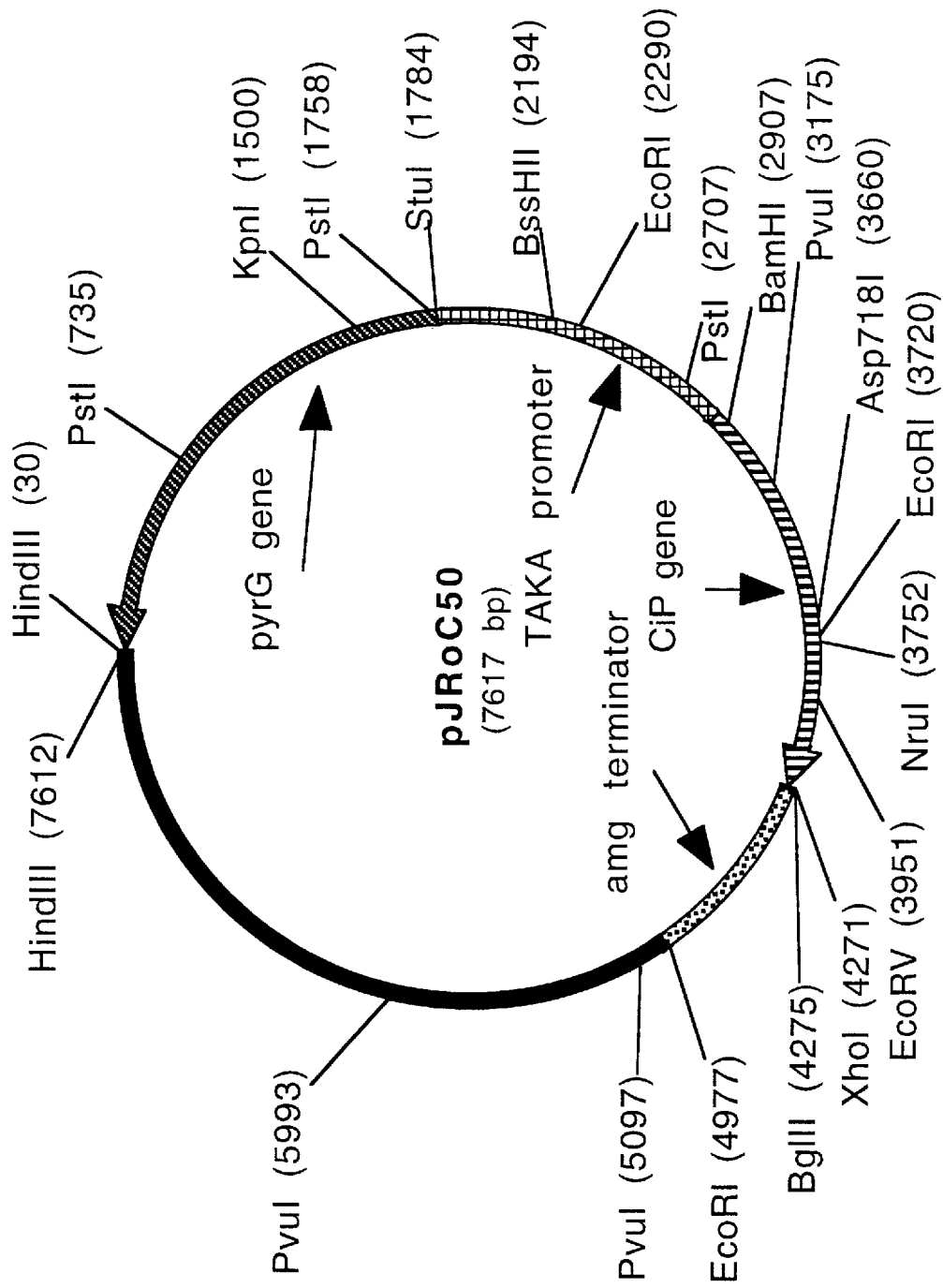
FIG. 10 shows a restriction map of plasmid pJRoC50.

The cDNA encoding the Coprinus cinereus peroxidase was excised from plasmid pJVi9 as a BamHI-XhoI fragment and cloned into plasmid pJeRS6 (FIG. 9) to produce plasmid pJRoC50 (FIG. 10) which contains pyrG as a selectable marker, the TAKA promoter, and the amdS terminator.

Transformants of Aspergillus oryzae strain HowB425 were made using 5 μg of purified plasmid pJRoC50 as described below with the following changes. The agar overlay was omitted and the protoplasts were plated directly on Minimal Medium plates. The transformation was conducted with protoplasts at a concentration of 2×10$^7$ protoplasts per ml. One hundred μl of protoplasts were placed on ice with 5 μg DNA for 30 minutes. One ml of SPTC (40% PEG 4000, 0.8M sorbitol, 0.05M Tris pH 8.0, 0.05M CaCl$_2$) was added and the protoplasts were incubated at 34° C. for 20 minutes. The transformation was plated directly onto plates containing Minimal medium. The Minimal medium (pH 6.5) was composed of 6 g of NaNO$_3$, 0.52 g of KCl, 1.52 g of KH$_2$PO$_4$, 1 ml of trace metals, 1 g of glucose, 500 mg of MgSO$_4$-7H$_2$O, 342.3 g of sucrose, and 20 g of Noble agar per liter. The trace metals solution (1000X) was composed of 22 g of ZnSO$_4$-7H$_2$O, 11 g of H$_3$BO$_3$, 5 g of MnCl$_2$-4H$_2$O, 5 g of FeSO$_4$-7H$_2$O, 1.6 g of CoCl$_2$-5H$_2$O, 1.6 g of (NH$_4$)$_6$Mo$_7$O$_{24}$, and 50 g of Na$_4$EDTA per liter. Plates were incubated 5–7 days at 34° C. Transformants were transferred to plates of the same medium and incubated 3–5 days at 37° C.

Sixty-six transformants were assayed for peroxidase activity using the following enzyme assay: 180 μl of substrate buffer {20 ml of 0.1M potassium phosphate—0.01% Tween—80 pH 7.0, 250 μl of 2,2'-azinobis(3-ethylbenzothiazoline-6-sulfonate) (ABTS) solution (22 mg/ml), and 2 μl of 30% hydrogen peroxide} were added to 20 μl of culture supernatant which was diluted 1:900, quickly followed by measurement of the absorbance at 405 nm at 25° C. using a Molecular Devices Thermomax Microplate Reader (Molecular Devices, Sunnyvale, Calif.). Measurements were recorded every 10 seconds over a 2 minute period with mixing and $V_{max}$ values were calculated using the SOFTmax program (Molecular Devices, Sunnyvale, Calif.). The peroxidase units (POXU) per ml were estimated using a standard curve constructed with a known amount of Cinereus coprinus peroxidase as a standard. A POXU was defined as the amount of enzyme that catalyzes the conversion of 1.0 μmole per minute of 0.88 mM $H_2O_2$, 1.67 mM ABTS, 0.1M phosphate pH 7.0 at 30C. The four transformants expressing the highest levels were spore purified by streaking spores and picking isolated colonies using the same plates under the same conditions described above.

Final evaluations were performed in shake flasks where approximately $5\times10^6$ spores of each transformant were inoculated into 25 ml of MY25 medium containing 1% yeast extract, 2.5% maltose, 0.2% urea, and 1X MY salts pH 6.5. 1X MY salts was composed of 2 g of $MgSO_4$–$7H_2O$, 2 g of $K_2PO_4$, 10 g of $KH_2PO_4$, 2 g of citric acid, 0.5 ml of trace metals solution and 1 ml of 10% $CaCl_2$–$2H_2O$ per liter. The trace metals solution was composed of 13.9 g of $FeSO_4$–$7H_2O$, 8.5 g of $MnSO_4$–$H_2O$, 14.28 g of $ZnSO_4$–$7H_2O$, 1.63 g of $CuSO_4$, 0.24 g of $NiCl_2$–$6H_2O$, and 3.0 g of citric acid per liter. Hemin was added to a final concentration of 0.01 mg/ml from a fresh 10 mg/ml stock prepared in 50 mM NaOH. The shake flasks were incubated at 34° C. and 200 rpm for 7 to 8 days. The best peroxidase producer was designated JRoC50.3.18A.

Example 8

Transformation of Aspergillus oryzae JRoC50.3.18A with pSE31

Aspergillus oryzae strain JRoC50.3.18A was transformed with pSE31 in order to determine whether overexpression of the hemA gene increased peroxidase production.

The transformation was conducted with protoplasts at a concentration of $2\times10^7$ protoplasts per ml. One hundred μl of protoplasts were incubated at 34° C. with 10 μg DNA and 200 μl of 60% PEG 4000—10 mM HEPES—10 mM $CaCl_2$ solution for 30 minutes. Three ml of SPTC (40% PEG 4000, 0.8M sorbitol, 0.05M Tris pH 8.0, 0.05M $CaCl_2$) were added and the protoplasts were plated directly onto COVE transformation plates (per liter: 0.52 g of KCl, 0.52 g of $MgSO_4$–$7H_2O$, 1.52 g of $KH_2PO_4$, 1 ml of trace metals solution as described in Example 7, 342.3 g of sucrose, 25 g of Noble agar, 10 ml of 1M acetamide, and 10 ml of 3M CsCl) for amdS transformations. Plates were incubated 5–7 days at 34° C. Transformants were transferred to plates of the same medium and incubated 3–5 days at 34° C. The transformants were then purified by streaking spores and picking isolated colonies using the same plates under the same conditions.

Example 9

Peroxidase production by hemA transformants

The transformants from Example 8 were inoculated into individual wells at approximately $1\times10^5$ spores per well of a 24-well microtiter plate containing 1 ml of quarter strength MY25 medium composed of 0.25% yeast extract, 0.63% maltose, and 0.05% urea pH 6.5, and 1X MY salts (see Example 7). The microtiter plates were incubated at 34° C. and 100 rpm in a humidity chamber for 5 days.

Peroxidase production levels were determined using the enzyme assay described in Example 7. The results of the microtiter plate tests demonstrate that the average POXU/ml of hemA transformants was 1.4-fold greater than the average of the vector only transformants, with the best hemA transformant showing a 1.6-fold increase in peroxidase production.

A minority (39%) of the hemA transformants show peroxidase levels similar to the majority of the vector only controls. PCR amplification using 50 ng of genomic DNA isolated as described in Example 1 from each transformant was performed as described in Example 2 except the primers hemA3' (see Example 4) and primer 5'-TCTCTTCCTTCCTGAATCCTC-3' (SEQ ID NO:15) were used. This analysis showed that the hemA transformants contain the expression cassette.

Eleven of the best hemA transformants obtained above were cultivated in shake flasks to better evaluate the effects on peroxidase production. For shake flask evaluations, approximately $5\times10^6$ spores of each transformant were inoculated into 25 ml of MY25 medium containing 1% yeast extract, 2.5% maltose, 0.2% urea, and 1X MY salts pH 6.5 (see Example 7). The shake flasks were incubated at 34° C. and 200 rpm for 7 to 8 days. Peroxidase assays were performed as described above.

The results demonstrated that five transformants, SE01-15, SE01-20, SE01-26, SE01-28 and SE01-32, produced peroxidase levels which were greater than the vector alone control strains, with three transformants expressing peroxidase at a level 1.9-fold greater than the average control peroxidase levels. The remaining six hemA transformants showed peroxidase levels which were comparable to control levels.

Transformant SE01-28 and a control strain SE05-18 (pBANe6 vector alone transformant) were grown in 2 liter fermentations using a standard fed-batch protocol which has high maltose syrup as carbon source. The batch and feed were supplemented with $FeCl_3$ to approximately 0.4 mM. Positive dissolved oxygen tension was maintained in both cultures with feed added at a rate of approximately 2 grams saccharide per liter per hour from day three to day eight. This level was reached in a step-wise manner over days two and three. Biomass in both cultures were approximately equal for the duration of the fermentation.

A 2-fold increase in peroxidase activity was observed with SE 01-28 over the control strain SE05-18. There was also a 2-fold increase in the polypeptide level for SE01-28 relative to the control strain SE05-18.

The overall results demonstrated that overexpression of the hemA gene resulted in a 2-fold increase in peroxidase yield. The data indicated further that hemA may represent a key regulatory point during heme biosynthesis in filamentous fungi which upon genetic manipulation can improve hemoprotein production in the absence of hemin supplementation.

DEPOSIT OF MICROORGANISMS

The following strain has been deposited according to the Budapest Treaty in the Agricultural Research Service Patent Culture Collection (NRRL), Northern Regional Research Laboratory, 1815 University Street, Peoria, Ill. 61604, U.S.A.

| Strain | Accession Number | Deposit Date |
|---|---|---|
| E. coli DH5α (pSE17) | NRRL B-21563 | April 22, 1996 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A substantially pure 5-aminolevulinic acid synthase obtained from an *Aspergillus oryzae* strain.

2. A 5-aminolevulinic acid synthase according to claim 1 which is obtained from *Aspergillus oryzae* IFO 4177 or a mutant strain thereof.

3. A 5-aminolevulinic acid synthase according to claim 1 which has an amino acid sequence set forth in SEQ ID NO:2.

4. A substaintially pure 5-aminolevulinic acid synthase which has an amino acid sequence which differs by no more than three amino acids from the amino acid sequence set forth in SEQ ID NO:2.

5. A 5-aminolevulinic acid synthase according to claim 4 which has an amino acid sequence which differs by two amino acids from the amino acid sequence set forth in SEQ ID NO:2.

6. A 5-aminolevulinic acid synthase according to claim 4 which has an amino acid sequence which differs by one amino acid from the amino acid sequence set forth in SEQ ID NO:2.

7. A 5-aminolevulinic acid synthase according to claim 1 which is encoded by a nucleic acid sequence which is capable of hybridizing under conditions of high stringency with a probe which hybridizes with the nucleic acid sequence set forth in SEQ ID NO: 1 under the conditions of high stringency.

8. A method for producing a 5-aminolevulinic acid synthase of claim 1 comprising
  (a) cultivating an *Aspergillus oryzae* strain to produce the 5-aminolevulinic acid synthase; and
  (b) recovering the 5-aminolevulinic acid synthase.

* * * * *

UNITED STATES PATENT AND TRADEMARK OFFICE
CERTIFICATE OF CORRECTION

PATENT NO. : 5,871,991
DATED : February 16, 1999
INVENTOR(S) : Elrod et al.

It is certified that error appears in the above-identified patent and that said Letters Patent is hereby corrected as shown below:

Col. 5, line 26: delete "373 1" and insert --3731--
Col. 10, line 49: delete "hema" and insert --hem$A$--
Col. 14, line 28: delete "Bimboim" and insert --Birnboim--

Signed and Sealed this

Seventh Day of December, 1999

Attest:

Q. TODD DICKINSON

*Attesting Officer*       *Acting Commissioner of Patents and Trademarks*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 4157 base pairs
( B ) TYPE: nucleic acid
( C ) STRANDEDNESS: single
( D ) TOPOLOGY: linear ( x i ) SEQUENCE DESCRIPTION: SEQ ID NO:1:

```
ACCATTGACT CTCAAGCTAT GGATCGTGCT CACCGTCTCG GCCAGACAAG ACAGGTCACG      60
GTGTATCGCC TGATTACTCG CGGCACCATT GAGGAGCGTA TTCGCAAGCG AGCTTTGCAG     120
AAGGAGGAAG TGCAGCGTGT CGTCATCTCA GGTGGCGCAG CTGGTGGGGT TGACTTCAAT     180
ACTCGCAACC GCGAGAGCCG AACCAAGGAC ATCGCCATGT GGCTGGCAGA TGATGAACAG     240
GCGGAGCTTA TTGAGCAAAA GGAGAAGGAA GCGCTGGACC GAGGCGAAGT GTTTGGCGCT     300
AGTAAAGGCG GGAAGAAGGC TGCTCAGAAG AGAAAGAGAG ATATCACGCT GGATGATATG     360
TATCATGAAG GTATGTGAAT CTGATCAAAG CTCTTCGTTC CGGGGAGGCT TCTGGAAATA     420
GTACTAACCG CGTCAATCTA TAGGCGAAGG GAACTTTGAC GATGCCAGTG CAAAGCCATC     480
AGGAGCGGCC ACTCCTGTGT CGACTGCAGA GAATTTAGGC ACCCCATCCT CCACGCCAGT     540
TCCTAAACGA GGACGTGGAA GGGGGACAGG AAAGGGCACG TCTAAAAGAG CCAAAACTAC     600
CAAGGAGAGA TTACGTCTCA TTGATGGCGA CGGAGGCTTA GGGCCTAGTT GATTTAATCG     660
ATCTGTGCCT CAATAATGGA CACGGCTGGT TATGGTCATG GCGTTCAGAG ATTGCATTTC     720
TTTCCCACCC TTTATCTTTC TTTCTTTCCT CTTAAACCCC TCTTTTTTGT TTTTCTTTTT     780
ATCGGACTTT ACTTGTGGGC AGCTTACGTT CTGCCTTGTA TTAACAGCAT ATATTCCTGA     840
TTCCTGATGT ACGAAGCGAT TTAAGAGTCA TTGAAGACGA AGGATGAAAC CCGTGGTAAT     900
CAGCCGATAA TGGCAAAGAG AAGGAGAAGA AAAAAATCAA GTGCGAGTTT TGAAATTGAT     960
GGCAAGATAG ACATTGTATC CTGTACCTGT TCTTGGGCTG TGACGGGGGG GGTGAAATTG    1020
ACGGTCATCA CCCGGCTATT ATTACTATTG TTGTACTGTA CATCCGGATC CTGCTGGTCT    1080
GTATCTAGTT AGGGCAATAT TCCCCGTCGC CAGGCCTCTT GGGTTATGAA TGATTTCATA    1140
```

```
GGTGAAGTTT   CGTATCCGTA   CGCACCGAGA   GATTTCTTAG   TATTACTTGT   ATTATGAAAA   1200
TGCACTTGCC   GAGTTAAGTC   CGCCGGCCAA   TCACGGCGGA   GGATATGGTA   AGCCGAAAAG   1260
TCTCGCCGAA   GTCCCCGACT   TACTCTTACT   GGAAGTGGCT   TAGTGCCCTC   AGCGCCCCCT   1320
CGCCCTCAGT   CCATCAGCCA   GATTGACTCT   TATTTCTCTC   TCCTCTTCGC   CGCGGGTGAC   1380
ATATCCCTCT   CCTTCTCCCT   CTCCCTCTTG   ACAACATTTC   ATCTTCGCTT   CCTTTTGTGA   1440
TATAGTCAGT   TTCGCTATCC   ATTGAAGCAT   CACTCATGGA   GTCTCTTCTC   CAGCAGTCCC   1500
GGGCGATGTG   CCCGTTCCTT   AAGCGCACAT   CTCCATCTTC   TCTGCGTACG   CTGGCAACCG   1560
CGACTCGACC   TAGCACTAGT   TCCGGTGGAG   GCACTATGTC   TAATCTCCAG   GTCATTGCCC   1620
GTCGCTGCCC   TGTCATGAGC   AAGGCTCTGG   CCGTGCAGAG   CGCTCGCATG   GCCGGTACCA   1680
AAAGATTCAC   CTCATGTGCT   GCCGGCATCA   CCGGTCTCGG   CAACAAGCAT   TGCCGTGCTC   1740
CTACTGGGAA   GAGAACCCTG   CACTCCACCT   CCGGTAACGG   CGCCAATGTG   AGCGCAGAGA   1800
TCTACAAGAA   CACCCAGCGA   GATCCCGCCG   GTTTCTCGAA   GATCAAGACC   CCTGCCAATG   1860
CTACCGCCGC   TGCCGCTACG   TCTGGCCCTC   GTCCAGAGGC   TCCCGTGGCG   AAGCCTTTCA   1920
ACTACAATTC   TTTCTACAAC   ACCGAATTGG   AAAAGAAACA   CAAGGACAAG   TCGTATCGCT   1980
ATTTCAACAA   CATCAATCGT   CTCGCTCAGG   AGTTTCCCCG   GGCTCACACC   ACATCTGCCG   2040
AGGAACGTGT   GACGGTCTGG   TGCTCGAACG   ATTATCTCGG   CATGGGCCGC   AACCCCGAGG   2100
TTCTGGCCAC   CATGCATAAG   ACATTGGACA   CCTACGGAGC   CGGTGCGGGA   GGTACTCGCA   2160
ACATTTCAGG   TCACAATCAA   CATGCCGTGA   GCCTGGAGAA   CACCCTGGCC   AAATTGCACG   2220
GCAAGGAGGC   GGCATTAGTC   TTCAGCTCAT   GCTTCGTGGC   TAACGATGCC   ACCCTCGCAA   2280
CCCTGGGTAG   CAAGTTGCCC   GACTGTGTTA   TTCTGTCCGA   TAGCCTGAAT   CATGCATCGA   2340
TGATTCAGGG   TATTCGCCAT   TCAGGCGCCA   AGAAAATGGT   TTTCAAGCAT   AATGATCTGG   2400
TCGACCTTGA   GGCCAAGTTG   GCAGCTCTAC   CTCTTCATGT   CCCCAAGATT   ATTGCATTCG   2460
AATCAGTTTA   TAGCATGTGC   GGATCTATTG   CCCCAATTGA   GAAGATCTGT   GATCTTGCAG   2520
ACAAGTACGG   TGCCATTACT   TTCCTGGATG   AAGTCCACGC   TGTGGGAATG   TACGGACCTC   2580
ACGGAGCAGG   TGTGGCAGAG   CACCTTGACT   ATGACATCTA   TGCTTCCCAA   GATACGGTCA   2640
ACCCGCGCAG   TACTAAGGGA   ACCGTGATGG   ACCGAATCGA   TATTATCACC   GGTACTCTGG   2700
GCAAGGCCTA   CGGATGTGTC   GGGGGCTACA   TTGCTGGATC   CGCTGCGATG   GTTGACACCA   2760
TCCGCTCCCT   CGCCCCTGGC   TTCATCTTCA   CCACGTCCTT   GCCGCCCGCC   ACCATGGCTG   2820
GTGCAGACAC   TGCTATCCAG   TACCAGGCTC   GTCACCAGGG   CGACCGCGTC   CTGCAGCAGT   2880
TGCACACCCG   CGCGGTCAAA   GCAGCTTTCA   AGGAGTTGGA   TATTCCTGTA   ATTCCCAACC   2940
CCTCCCATAT   CATTCCGCTC   CTGGTTGGGG   ATGCCGAGGT   TGCTAAGAAG   GCCTCGGACA   3000
AGCTTCTGGA   GGAGCATGGA   ATTTATGTAC   AAGCCATCAA   CTACCAACC   GTGCCTCGGG   3060
GTGAAGAGCG   GCTTCGTATC   ACGCCCACCC   CGGGACATAT   CAAGGAGCAC   CGCGACCACC   3120
TGGTGCAAGC   CGTCCAAACA   GTCTGGAACG   AACTGGGCAT   CAAACGCACC   AGCGATTGGG   3180
AAGCGCAAGG   CGGCTTCGTC   GGCGTGGGTG   TCGATGGCGC   CGAGGCTGAG   AACCAGCCGA   3240
TTTGGAATGA   TGTGCAGCTG   GGGCTGAAGG   AAAACGAAGC   CATTGAGGCT   GCTGTGGAAC   3300
GCGAGTTTGC   CGAGGCCCCC   ATGCGGACCG   CCACCCGTCC   TGCCGCGGCT   GCTGCTTCGT   3360
CAATCCCGGT   GGGTGTGGCT   GCCTGAAGTG   GCTGCCCGCA   TGTGAGCTGA   AATCGACGTG   3420
GAATTCTATA   CACACACACA   CACACACACA   CACACACACA   CACACACACA   CACACACACA   3480
CACACACACA   CACACACACT   AACACACACT   ATGTTATAAA   TTCCACATCC   ACTCCTTTGT   3540
```

| | | | | | | |
|---|---|---|---|---|---|---|
| CCCTTGTTGG | ACGTAATTGG | TATTTGGACT | ATTAGTTAGA | ACCAGTCAGT | CGTTACCATG | 3600 |
| TGTTTCGGTT | CGACTCGAAA | TCTGACATGT | TGTCTGCCCC | CATGCCACTT | CATCTCCTCC | 3660 |
| GTAACCGCAG | GGCTTCAAAT | ACACTGCCCA | GTAATTGTAG | TCAATATAGC | AGTTAACTAA | 3720 |
| CCTTCACCAA | TTTCCTAATA | ACAATAGAAG | GGGCCATACA | CGCAGTACCA | AAGATCACCT | 3780 |
| ACCTCCGATC | AATATCCGAA | CCTCAGGCTA | CATACATCAA | GTCGCATTAA | TCGATTCCGA | 3840 |
| CCTCTGTTTA | TCCCTGAAAA | TAACTAAGAT | CATGATCTAC | GTTTGGTAAG | TGGGACACCT | 3900 |
| ACCTACACTG | GGAGGTATTG | AATAAAGGCA | TCATTCATAT | AGTCACAAGA | TGCCAGGGCC | 3960 |
| AATTCATGAT | ATGGATAGCT | ACTTCCAAAC | ATAATTCAGA | GGTATCATTC | TGCTCTTCAG | 4020 |
| ACAGTTCTTC | TCGAAGATCA | GTAGGAGCCA | GTTTTGACCA | TTAACTTGTA | ATGTAATTGC | 4080 |
| GATTGTAGTA | GATCCGAGAT | CCATTCACTT | TCTAAGGGTT | AATTGATTCA | TTTTACTGAT | 4140 |
| ACCTCACCCA | CCATATT | | | | | 4157 |

(2) INFORMATION FOR SEQ ID NO:2:

(i) SEQUENCE CHARACTERISTICS:
        (A) LENGTH: 636 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Glu Ser Leu Leu Gln Gln Ser Arg Ala Met Cys Pro Phe Leu Lys
  1               5                  10                  15

Arg Thr Ser Pro Ser Ser Leu Arg Thr Leu Ala Thr Ala Thr Arg Pro
                 20                  25                  30

Ser Thr Ser Ser Gly Gly Gly Thr Met Ser Asn Leu Gln Val Ile Ala
             35                  40                  45

Arg Arg Cys Pro Val Met Ser Lys Ala Leu Ala Val Gln Ser Ala Arg
         50                  55                  60

Met Ala Gly Thr Lys Arg Phe Thr Ser Cys Ala Ala Gly Ile Thr Gly
 65                  70                  75                  80

Leu Gly Asn Lys His Cys Arg Ala Pro Thr Gly Lys Arg Thr Leu His
                 85                  90                  95

Ser Thr Ser Gly Asn Gly Ala Asn Val Ser Ala Glu Ile Tyr Lys Asn
                100                 105                 110

Thr Gln Arg Asp Pro Ala Gly Phe Ser Lys Ile Lys Thr Pro Ala Asn
            115                 120                 125

Ala Thr Ala Ala Ala Ala Thr Ser Gly Pro Arg Pro Glu Ala Pro Val
        130                 135                 140

Ala Lys Pro Phe Asn Tyr Asn Ser Phe Tyr Asn Thr Glu Leu Glu Lys
145                 150                 155                 160

Lys His Lys Asp Lys Ser Tyr Arg Tyr Phe Asn Asn Ile Asn Arg Leu
                165                 170                 175

Ala Gln Glu Phe Pro Arg Ala His Thr Thr Ser Ala Glu Glu Arg Val
            180                 185                 190

Thr Val Trp Cys Ser Asn Asp Tyr Leu Gly Met Gly Arg Asn Pro Glu
        195                 200                 205

Val Leu Ala Thr Met His Lys Thr Leu Asp Thr Tyr Gly Ala Gly Ala
        210                 215                 220
```

| Gly | Gly | Thr | Arg | Asn | Ile | Ser | Gly | His | Asn | Gln | His | Ala | Val | Ser | Leu |
| 225 | | | | 230 | | | | 235 | | | | | | | 240 |
| Glu | Asn | Thr | Leu | Ala | Lys | Leu | His | Gly | Lys | Glu | Ala | Ala | Leu | Val | Phe |
| | | | | 245 | | | | 250 | | | | | | 255 | |
| Ser | Ser | Cys | Phe | Val | Ala | Asn | Asp | Thr | Leu | Ala | Thr | Leu | Gly | Ser |
| | | | 260 | | | | | 265 | | | | 270 | | |
| Lys | Leu | Pro | Asp | Cys | Val | Ile | Leu | Ser | Asp | Ser | Leu | Asn | His | Ala | Ser |
| | | 275 | | | | | 280 | | | | | 285 | | | |
| Met | Ile | Gln | Gly | Ile | Arg | His | Ser | Gly | Ala | Lys | Lys | Met | Val | Phe | Lys |
| | | 290 | | | | 295 | | | | | 300 | | | | |
| His | Asn | Asp | Leu | Val | Asp | Leu | Glu | Ala | Lys | Leu | Ala | Ala | Leu | Pro | Leu |
| 305 | | | | | 310 | | | | 315 | | | | | | 320 |
| His | Val | Pro | Lys | Ile | Ile | Ala | Phe | Glu | Ser | Val | Tyr | Ser | Met | Cys | Gly |
| | | | | 325 | | | | | 330 | | | | | 335 | |
| Ser | Ile | Ala | Pro | Ile | Glu | Lys | Ile | Cys | Asp | Leu | Ala | Asp | Lys | Tyr | Gly |
| | | | 340 | | | | | 345 | | | | | 350 | | |
| Ala | Ile | Thr | Phe | Leu | Asp | Glu | Val | His | Ala | Val | Gly | Met | Tyr | Gly | Pro |
| | | | 355 | | | | | 360 | | | | | 365 | | |
| His | Gly | Ala | Gly | Val | Ala | Glu | His | Leu | Asp | Tyr | Asp | Ile | Tyr | Ala | Ser |
| | 370 | | | | | 375 | | | | | 380 | | | | |
| Gln | Asp | Thr | Val | Asn | Pro | Arg | Ser | Thr | Lys | Gly | Thr | Val | Met | Asp | Arg |
| 385 | | | | | 390 | | | | | 395 | | | | | 400 |
| Ile | Asp | Ile | Ile | Thr | Gly | Thr | Leu | Gly | Lys | Ala | Tyr | Gly | Cys | Val | Gly |
| | | | | 405 | | | | | 410 | | | | | 415 | |
| Gly | Tyr | Ile | Ala | Gly | Ser | Ala | Ala | Met | Val | Asp | Thr | Ile | Arg | Ser | Leu |
| | | | 420 | | | | | 425 | | | | | 430 | | |
| Ala | Pro | Gly | Phe | Ile | Phe | Thr | Thr | Ser | Leu | Pro | Pro | Ala | Thr | Met | Ala |
| | | 435 | | | | | 440 | | | | | 445 | | | |
| Gly | Ala | Asp | Thr | Ala | Ile | Gln | Tyr | Gln | Ala | Arg | His | Gln | Gly | Asp | Arg |
| | 450 | | | | | 455 | | | | | 460 | | | | |
| Val | Leu | Gln | Gln | Leu | His | Thr | Arg | Ala | Val | Lys | Ala | Ala | Phe | Lys | Glu |
| 465 | | | | | 470 | | | | | 475 | | | | | 480 |
| Leu | Asp | Ile | Pro | Val | Ile | Pro | Asn | Pro | Ser | His | Ile | Ile | Pro | Leu | Leu |
| | | | | 485 | | | | | 490 | | | | | 495 | |
| Val | Gly | Asp | Ala | Glu | Val | Ala | Lys | Lys | Ala | Ser | Asp | Lys | Leu | Leu | Glu |
| | | | 500 | | | | | 505 | | | | | 510 | | |
| Glu | His | Gly | Ile | Tyr | Val | Gln | Ala | Ile | Asn | Tyr | Pro | Thr | Val | Pro | Arg |
| | | 515 | | | | | 520 | | | | | 525 | | | |
| Gly | Glu | Glu | Arg | Leu | Arg | Ile | Thr | Pro | Thr | Pro | Gly | His | Ile | Lys | Glu |
| | 530 | | | | | 535 | | | | | 540 | | | | |
| His | Arg | Asp | His | Leu | Val | Gln | Ala | Val | Gln | Thr | Val | Trp | Asn | Glu | Leu |
| 545 | | | | | 550 | | | | | 555 | | | | | 560 |
| Gly | Ile | Lys | Arg | Thr | Ser | Asp | Trp | Glu | Ala | Gln | Gly | Gly | Phe | Val | Gly |
| | | | | 565 | | | | | 570 | | | | | 575 | |
| Val | Gly | Val | Asp | Gly | Ala | Glu | Ala | Glu | Asn | Gln | Pro | Ile | Trp | Asn | Asp |
| | | | 580 | | | | | 585 | | | | | 590 | | |
| Val | Gln | Leu | Gly | Leu | Lys | Glu | Asn | Glu | Ala | Ile | Glu | Ala | Ala | Val | Glu |
| | | 595 | | | | | 600 | | | | | 605 | | | |
| Arg | Glu | Phe | Ala | Glu | Ala | Pro | Met | Arg | Thr | Ala | Thr | Arg | Pro | Ala | Ala |
| | 610 | | | | | 615 | | | | | 620 | | | | |
| Ala | Ala | Ala | Ser | Ser | Ile | Pro | Val | Gly | Val | Ala | Ala |
| 625 | | | | | 630 | | | | 635 | | |

(2) INFORMATION FOR SEQ ID NO:3:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:3:

TTTATGATGG AGGCCCTTCT CCAGCAGTCT C        31

( 2 ) INFORMATION FOR SEQ ID NO:4:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( x i ) SEQUENCE DESCRIPTION: SEQ ID NO:4:

CTATGCATTT AAGCAGCAGC CGCGACTGG        29

( 2 ) INFORMATION FOR SEQ ID NO:5:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( x i ) SEQUENCE DESCRIPTION: SEQ ID NO:5:

TCATTTAAAT GATGGAGTCT CTTCTCC        27

( 2 ) INFORMATION FOR SEQ ID NO:6:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:6:

TCTTAATTAA TCAGCTCACA TGCGGG        26

( 2 ) INFORMATION FOR SEQ ID NO:7:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:7:

GCGCGAATTC GTNGGNATNG GNATNAAYCA YGG        33

( 2 ) INFORMATION FOR SEQ ID NO:8:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:8:

GCGGATCCGG NGGRCARTTN GACAT        25

( 2 ) INFORMATION FOR SEQ ID NO:9:

( i ) SEQUENCE CHARACTERISTICS:

( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCGAATTCAC NCCNCARGTN TTYGAYAC 28

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GCGGATCCRA AYTCNCCNGG RAANGG 26

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GCGCGAATTC TGGCARTCNA C 21

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GCGCGAATTC TGGCARAGNA TG 22

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GGATCCGACA TYTTNGCCAT NGC 23

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTYTCRATRT AGAAYTG 17

( 2 ) INFORMATION FOR SEQ ID NO:15:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:15:

TCTCTTCCTT CCTGAATCCT C    21

(2) INFORMATION FOR SEQ ID NO:16:

(i) SEQUENCE CHARACTERISTICS:
(A) LENGTH: 649 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:16:

| Met | Glu | Ala | Leu | Leu | Gln | Gln | Ser | Arg | Ala | Met | Cys | Pro | Phe | Leu | Lys |
|-----|-----|-----|-----|-----|-----|-----|-----|-----|-----|-----|-----|-----|-----|-----|-----|
| 1 | | | | 5 | | | | | 10 | | | | | 15 | |
| Arg | Ser | Ser | Pro | Asn | Thr | Leu | Arg | Ser | Leu | Ala | Thr | Ala | Thr | Arg | Pro |
| | | | 20 | | | | | 25 | | | | | 30 | | |
| Ser | Thr | Ser | Pro | Gly | Gly | Gly | Thr | Met | Thr | Asn | Leu | Gln | Arg | Ile | Ala |
| | | 35 | | | | | 40 | | | | | 45 | | | |
| Arg | Arg | Cys | Pro | Val | Met | Ser | Lys | Ala | Leu | Ala | Val | Gln | Ser | Ala | Arg |
| | 50 | | | | | 55 | | | | | 60 | | | | |
| Met | Thr | Gly | Thr | Lys | Arg | Phe | Thr | Ser | Ser | Ala | Ala | Gly | Val | Pro | Gly |
| 65 | | | | | 70 | | | | | 75 | | | | | 80 |
| Ala | Gly | Ala | Gly | Thr | Pro | Lys | Pro | Thr | Arg | Gly | Ser | Pro | Gly | Lys | Arg |
| | | | | 85 | | | | | 90 | | | | | 95 | |
| Ala | Leu | His | Ser | Thr | Gly | Gly | Asn | Gly | Ala | Asn | Met | Ser | Thr | Glu | Phe |
| | | | 100 | | | | | 105 | | | | | 110 | | |
| His | Lys | Gly | Ala | Gln | Gln | Ile | His | Pro | Gly | Leu | Ser | Asn | Ala | Thr | Arg |
| | | | 115 | | | | 120 | | | | | 125 | | | |
| Ser | His | Val | Gly | Ala | Ser | Ala | Thr | Val | Ser | Gly | Pro | Thr | Pro | Arg | Ala |
| | 130 | | | | | 135 | | | | | 140 | | | | |
| Pro | Val | Ala | Ala | Pro | Phe | Asp | Tyr | Asp | Ala | Phe | Tyr | Asn | Ala | Glu | Leu |
| 145 | | | | | 150 | | | | | 155 | | | | | 160 |
| Gln | Lys | Lys | His | Gln | Asp | Lys | Ser | Tyr | Arg | Tyr | Phe | Asn | Asn | Ile | Asn |
| | | | | 165 | | | | | 170 | | | | | 175 | |
| Arg | Leu | Ala | Gln | Glu | Phe | Pro | Arg | Ala | His | Thr | Ala | Ser | Lys | Asp | Glu |
| | | | | 180 | | | | | 185 | | | | | 190 | |
| Lys | Val | Thr | Val | Trp | Cys | Ser | Asn | Asp | Tyr | Leu | Gly | Met | Gly | Arg | Asn |
| | | | 195 | | | | | 200 | | | | | 205 | | |
| Pro | Glu | Val | Leu | Ala | Thr | Met | His | Lys | Thr | Leu | Asp | Thr | Tyr | Gly | Ala |
| | 210 | | | | | 215 | | | | | 220 | | | | |
| Gly | Ala | Gly | Gly | Thr | Arg | Asn | Ile | Ser | Gly | His | Asn | Gln | His | Ala | Val |
| 225 | | | | | 230 | | | | | 235 | | | | | 240 |
| Ser | Leu | Glu | Asn | Thr | Leu | Ala | Lys | Leu | His | Gly | Lys | Glu | Ala | Ala | Leu |
| | | | | 245 | | | | | 250 | | | | | 255 | |
| Val | Phe | Ser | Ser | Cys | Phe | Val | Ala | Asn | Asp | Ala | Thr | Leu | Ala | Thr | Leu |
| | | | 260 | | | | | 265 | | | | | 270 | | |
| Gly | Ser | Lys | Met | Pro | Asp | Cys | Val | Ile | Leu | Ser | Asp | Ser | Leu | Asn | His |
| | | 275 | | | | | 280 | | | | | 285 | | | |
| Ala | Ser | Met | Ile | Gln | Gly | Ile | Arg | His | Ser | Gly | Arg | Lys | Lys | Met | Val |
| | 290 | | | | | 295 | | | | | 300 | | | | |
| Phe | Lys | His | Asn | Asp | Leu | Val | Asp | Leu | Glu | Thr | Lys | Leu | Ala | Ser | Leu |

|     |     |     |     |     |     |     |     |     |     |     |     |     |     |     |     |
|-----|-----|-----|-----|-----|-----|-----|-----|-----|-----|-----|-----|-----|-----|-----|-----|
| 305 |     |     |     | 310 |     |     |     | 315 |     |     |     | 320 |     |     |     |
| Pro | Leu | His | Val | Pro 325 | Lys | Ile | Ile | Ala | Phe 330 | Glu | Ser | Val | Tyr | Ser 335 | Met |
| Cys | Gly | Ser | Ile 340 | Ala | Pro | Ile | Glu | Ala 345 | Ile | Cys | Asp | Leu | Ala 350 | Asp | Lys |
| Tyr | Gly | Ala | Ile 355 | Thr | Phe | Leu | Asp | Glu 360 | Val | His | Ala | Val | Gly 365 | Met | Tyr |
| Gly | Pro 370 | His | Gly | Ala | Gly | Val 375 | Ala | Glu | His | Leu | Asp 380 | Tyr | Glu | Ile | Tyr |
| Ala 385 | Ser | Gln | Asp | Thr | Ala | Asn 390 | Pro | Leu | Ser | Thr | Lys 395 | Gly | Thr | Val | Met 400 |
| Asp | Arg | Ile | Asn | Ile 405 | Ile | Thr | Gly | Thr | Leu 410 | Gly | Lys | Ala | Tyr | Gly 415 | Cys |
| Val | Gly | Gly | Tyr 420 | Ile | Ala | Gly | Ser | Ala 425 | Ala | Leu | Val | Asp | Thr 430 | Ile | Arg |
| Ser | Leu | Ala 435 | Pro | Gly | Phe | Ile | Phe 440 | Thr | Thr | Ser | Leu | Pro 445 | Pro | Ala | Thr |
| Met | Ala | Gly 450 | Ala | Asp | Thr | Ala 455 | Ile | Arg | Tyr | Gln | Ala 460 | Arg | His | Gln | Gln |
| Asp 465 | Arg | Ile | Leu | Gln | Gln 470 | Leu | His | Thr | Arg | Ala 475 | Val | Lys | Gln | Ser | Phe 480 |
| Lys | Asp | Leu | Asp | Ile 485 | Pro | Val | Ile | Pro | Asn 490 | Pro | Ser | His | Ile | Val 495 | Pro |
| Leu | Leu | Val | Gly 500 | Asp | Ala | Glu | Leu | Ala 505 | Lys | Gln | Ala | Ser | Asp 510 | Lys | Leu |
| Leu | Glu | Glu | His 515 | Gly | Ile | Tyr | Val | Gln 520 | Ala | Ile | Asn | Tyr | Pro 525 | Thr | Val |
| Pro | Arg 530 | Gly | Glu | Glu | Arg | Leu 535 | Arg | Ile | Thr | Pro | Thr 540 | Pro | Gly | His | Thr |
| Gln 545 | Glu | Leu | Arg | Asp | His 550 | Leu | Val | Glu | Ala | Val 555 | Asn | Thr | Val | Trp | Asn 560 |
| Asp | Leu | Gly | Ile | Lys 565 | Arg | Ala | Ser | Asp | Trp 570 | Lys | Ala | Met | Gly | Gly 575 | Phe |
| Val | Gly | Val | Gly 580 | Val | Glu | Ala | Ala | Glu 585 | Leu | Glu | Asn | Gln | Pro 590 | Ile | Trp |
| Thr | Asp | Ala 595 | Gln | Leu | Asn | Met | Arg 600 | Pro | Asp | Glu | Thr | Leu 605 | Glu | Ala | Ala |
| Val | Glu | Arg 610 | Glu | Phe | Gln | Ala 615 | Ala | Val | Pro | Gly | Met 620 | Lys | Ala | Gly | Gly |
| Ala 625 | Lys | Ala | Lys | Pro | Val 630 | Gly | Ser | Ile | Ala | Ala 635 | Asn | Pro | Ile | Gly | Ala 640 |
| Ser | Ile | Pro | Val | Ala 645 | Ala | Ala | Ala | Glx |     |     |     |     |     |     |     |

(2) INFORMATION FOR SEQ ID NO:17:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

|     |     |     |     |     |     |     |     |     |     |     |     |     |     |     |     |
|-----|-----|-----|-----|-----|-----|-----|-----|-----|-----|-----|-----|-----|-----|-----|-----|
| Met 1 | Gln | Arg | Ser | Ile 5 | Phe | Ala | Arg | Phe | Gly 10 | Asn | Ser | Ser | Ala | Ala 15 | Val |

| | | | | | | | | | | | | | | |
|---|---|---|---|---|---|---|---|---|---|---|---|---|---|---|
|Ser|Thr|Leu|Asn<br>20|Arg|Leu|Ser|Thr<br>25|Ala|Ala|Pro|His|Ala|Lys<br>30|Asn|
|Gly|Tyr|Ala<br>35|Thr|Ala|Thr|Gly<br>40|Ala|Ala|Ala|Ala|Thr<br>45|Ala|Thr||
|Ala|Ser<br>50|Ser|Thr|His|Ala<br>55|Ala|Ala|Ala|Ala<br>60|Ala|Ala|Asn|His||
|Ser<br>65|Thr|Gln|Glu|Ser|Gly<br>70|Phe|Asp|Tyr|Glu|Gly<br>75|Leu|Ile|Asp|Ser|Glu<br>80|
|Leu|Gln|Lys|Lys|Arg<br>85|Leu|Asp|Lys|Ser|Tyr<br>90|Arg|Tyr|Phe|Asn|Asn<br>95|Ile|
|Asn|Arg|Leu|Ala<br>100|Lys|Glu|Phe|Pro|Leu<br>105|Ala|His|Arg|Gln|Arg<br>110|Glu|Ala|
|Asp|Lys|Val<br>115|Thr|Val|Trp|Cys|Ser<br>120|Asn|Asp|Tyr|Leu|Ala<br>125|Leu|Ser|Lys|
|His|Pro<br>130|Glu|Val|Leu|Asp|Ala<br>135|Met|His|Lys|Thr|Ile<br>140|Asp|Lys|Tyr|Gly|
|Cys<br>145|Gly|Ala|Gly|Gly|Thr<br>150|Arg|Asn|Ile|Ala|Gly<br>155|His|Asn|Ile|Pro|Thr<br>160|
|Leu|Asn|Leu|Glu|Ala<br>165|Glu|Leu|Ala|Thr|Leu<br>170|His|Lys|Lys|Glu|Gly<br>175|Ala|
|Leu|Val|Phe|Ser<br>180|Ser|Cys|Tyr|Val|Ala<br>185|Asn|Asp|Ala|Val|Leu<br>190|Ser|Leu|
|Leu|Gly|Gln|Lys<br>195|Met|Lys|Asp|Leu|Val<br>200|Ile|Phe|Ser|Asp|Glu<br>205|Leu|Asn|
|His|Ala|Ser|Met<br>210|Ile|Val|Gly|Ile<br>215|Lys|His|Ala|Asn|Val<br>220|Lys|Lys|His|
|Ile<br>225|Phe|Lys|His|Asn|Asp<br>230|Leu|Asn|Glu|Leu|Glu<br>235|Gln|Leu|Leu|Gln|Ser<br>240|
|Tyr|Pro|Lys|Ser|Val<br>245|Pro|Lys|Leu|Ile|Ala<br>250|Phe|Glu|Ser|Val|Tyr<br>255|Ser|
|Met|Ala|Gly|Ser<br>260|Val|Ala|Asp|Ile|Glu<br>265|Lys|Ile|Cys|Asp|Leu<br>270|Ala|Asp|
|Lys|Tyr|Gly<br>275|Ala|Leu|Thr|Phe|Leu<br>280|Asp|Glu|Val|His|Ala<br>285|Val|Gly|Leu|
|Tyr|Gly<br>290|Pro|His|Gly|Ala|Gly<br>295|Val|Ala|Glu|His|Cys<br>300|Asp|Phe|Glu|Ser|
|His<br>305|Arg|Ala|Ser|Gly|Ile<br>310|Ala|Thr|Pro|Lys|Thr<br>315|Asn|Asp|Lys|Gly|Gly<br>320|
|Ala|Lys|Thr|Val|Met<br>325|Asp|Arg|Val|Asp|Met<br>330|Ile|Thr|Gly|Thr|Leu<br>335|Gly|
|Lys|Ser|Phe|Gly<br>340|Ser|Val|Gly|Gly|Tyr<br>345|Val|Ala|Ala|Ser|Arg<br>350|Lys|Leu|
|Ile|Asp|Trp|Phe<br>355|Arg|Ser|Phe|Ala|Pro<br>360|Gly|Phe|Ile|Phe|Thr<br>365|Thr|Thr|
|Leu|Pro|Pro<br>370|Ser|Val|Met|Ala|Gly<br>375|Ala|Thr|Ala|Ala|Ile<br>380|Arg|Tyr|Gln|
|Arg<br>385|Cys|His|Ile|Asp|Leu<br>390|Arg|Thr|Ser|Gln|Gln<br>395|Lys|His|Thr|Met|Tyr<br>400|
|Val|Lys|Lys|Ala|Phe<br>405|His|Glu|Leu|Gly|Ile<br>410|Pro|Val|Ile|Pro<br>415|Asn|Pro|
|Ser|His|Ile|Val<br>420|Pro|Val|Leu|Ile|Gly<br>425|Asn|Ala|Asp|Leu|Ala<br>430|Lys|Gln|
|Ala|Ser|Asp|Ile|Leu|Ile|Asn|Lys|His|Gln|Ile|Tyr|Val|Gln|Ala|Ile|

435                              440                              445

Asn   Phe   Pro   Thr   Val   Ala   Arg   Gly   Thr   Glu   Arg   Leu   Arg   Ile   Thr   Pro
      450                           455                     460

Thr   Pro   Gly   His   Thr   Asn   Asp   Leu   Ser   Asp   Ile   Leu   Ile   Asn   Ala   Val
465                           470                           475                              480

Asp   Asp   Val   Phe   Asn   Glu   Leu   Gln   Leu   Pro   Arg   Val   Arg   Asp   Trp   Glu
                        485                           490                           495

Ser   Gln   Gly   Gly   Leu   Leu   Gly   Val   Gly   Glu   Ser   Gly   Phe   Val   Glu   Glu
                  500                     505                           510

Ser   Asn   Leu   Trp   Thr   Ser   Ser   Gln   Leu   Ser   Leu   Thr   Asn   Asp   Asp   Leu
            515                           520                           525

Asn   Pro   Asn   Val   Arg   Asp   Pro   Ile   Val   Lys   Gln   Leu   Glu   Val   Ser   Ser
      530                     535                           540

Gly   Ile   Lys   Gln
545

( 2 ) INFORMATION FOR SEQ ID NO:18:

( i ) SEQUENCE CHARACTERISTICS:
                ( A ) LENGTH: 587 amino acids
                ( B ) TYPE: amino acid
                ( C ) STRANDEDNESS: single
                ( D ) TOPOLOGY: linear ( i i ) MOLECULE TYPE: None ( x i ) SEQUENCE DESCRIPTION: SEQ ID NO:18:

Met   Val   Thr   Ala   Ala   Met   Leu   Leu   Gln   Cys   Cys   Pro   Val   Leu   Ala   Arg
1                       5                       10                          15

Gly   Pro   Thr   Ser   Leu   Leu   Gly   Lys   Val   Lys   Thr   His   Gln   Phe   Leu
                  20                          25                          30

Phe   Gly   Ile   Gly   Arg   Cys   Pro   Ile   Leu   Ala   Thr   Gln   Gly   Pro   Asn   Cys
            35                          40                          45

Ser   Gln   Ile   His   Leu   Lys   Ala   Thr   Lys   Ala   Gly   Gly   Asp   Ser   Pro   Ser
      50                          55                          60

Trp   Ala   Lys   Gly   His   Cys   Pro   Phe   Met   Leu   Ser   Glu   Leu   Gln   Asp   Gly
65                          70                          75                              80

Lys   Ser   Lys   Ile   Val   Gln   Lys   Ala   Ala   Pro   Glu   Val   Gln   Glu   Asp   Val
                  85                          90                              95

Lys   Ala   Phe   Lys   Thr   Asp   Leu   Pro   Ser   Ser   Leu   Val   Ser   Val   Ser   Leu
                  100                         105                           110

Arg   Lys   Pro   Phe   Ser   Gly   Pro   Gln   Glu   Gln   Gln   Ile   Ser   Gly   Lys
            115                         120                           125

Val   Thr   His   Leu   Ile   Gln   Asn   Asn   Met   Pro   Gly   Asn   Tyr   Val   Phe   Ser
      130                         135                           140

Tyr   Asp   Gln   Phe   Phe   Arg   Asp   Lys   Ile   Met   Glu   Lys   Lys   Gln   Asp   His
145                         150                           155                             160

Thr   Tyr   Arg   Val   Phe   Lys   Thr   Val   Asn   Arg   Trp   Ala   Asp   Ala   Tyr   Pro
                        165                         170                             175

Phe   Ala   Gln   His   Phe   Phe   Glu   Ala   Ser   Val   Ala   Ser   Lys   Asp   Val   Ser
                  180                         185                           190

Val   Trp   Cys   Ser   Asn   Asp   Tyr   Leu   Gly   Met   Ser   Arg   His   Pro   Gln   Val
            195                         200                           205

Leu   Gln   Ala   Thr   Gln   Glu   Thr   Leu   Gln   Arg   His   Gly   Ala   Gly   Ala   Gly
      210                         215                           220

Gly   Thr   Arg   Asn   Ile   Ser   Gly   Thr   Ser   Lys   Phe   His   Val   Glu   Leu   Glu
225                         230                           235                             240

```
Gln Glu Leu Ala Glu Leu His Gln Lys Asp Ser Ala Leu Leu Phe Ser
            245                 250                 255
Ser Cys Phe Val Ala Asn Asp Ser Thr Leu Phe Thr Leu Ala Lys Ile
            260                 265                 270
Leu Pro Gly Cys Glu Ile Tyr Ser Asp Ala Gly Asn His Ala Ser Met
            275                 280                 285
Ile Gln Gly Ile Arg Asn Ser Gly Ala Ala Lys Phe Val Phe Arg His
        290                 295                 300
Asn Asp Pro Asp His Leu Lys Lys Leu Leu Glu Lys Ser Asn Pro Lys
305                     310                 315                 320
Ile Pro Lys Ile Val Ala Phe Glu Thr Val His Ser Met Asp Gly Ala
            325                 330                 335
Ile Cys Pro Leu Glu Glu Leu Cys Asp Val Ser His Gln Tyr Gly Ala
            340                 345                 350
Leu Thr Phe Val Asp Glu Val His Ala Val Gly Leu Tyr Gly Ser Arg
            355                 360                 365
Gly Ala Gly Ile Gly Glu Arg Asp Gly Ile Met His Lys Ile Asp Ile
        370                 375                 380
Ile Ser Gly Thr Leu Gly Lys Ala Phe Gly Cys Val Gly Gly Tyr Ile
385                     390                 395                 400
Ala Ser Thr Arg Asp Leu Val Asp Met Val Arg Ser Tyr Ala Ala Gly
                405                 410                 415
Phe Ile Phe Thr Thr Ser Leu Pro Pro Met Val Leu Ser Gly Ala Leu
            420                 425                 430
Glu Ser Val Arg Leu Leu Lys Gly Glu Glu Gly Gln Ala Leu Arg Arg
            435                 440                 445
Ala His Gln Arg Asn Val Lys His Met Arg Gln Leu Leu Met Asp Arg
    450                     455                 460
Gly Leu Pro Val Ile Pro Cys Pro Ser His Ile Ile Pro Ile Arg Val
465                     470                 475                 480
Gly Asn Ala Ala Leu Asn Ser Lys Leu Cys Asp Leu Leu Leu Ser Lys
                485                 490                 495
His Gly Ile Tyr Val Gln Ala Ile Asn Tyr Pro Thr Val Pro Arg Gly
            500                 505                 510
Glu Glu Leu Leu Arg Leu Ala Pro Ser Pro His His Ser Pro Gln Met
            515                 520                 525
Met Glu Asp Phe Val Glu Lys Leu Leu Leu Ala Trp Thr Ala Val Gly
        530                 535                 540
Leu Pro Leu Gln Asp Val Ser Val Ala Ala Cys Asn Phe Cys Arg Arg
545                     550                 555                 560
Pro Val His Phe Glu Leu Met Ser Glu Trp Glu Arg Ser Tyr Phe Gly
                565                 570                 575
Asn Met Gly Pro Gln Tyr Val Thr Thr Tyr Ala
            580                 585
```